United States Patent
Aizawa et al.

(10) Patent No.: US 7,746,461 B2
(45) Date of Patent: Jun. 29, 2010

(54) OPTICAL DEFECT INSPECTION APPARATUS

(75) Inventors: Noriyuki Aizawa, Hitachinaka (JP); Hiroyuki Kawakami, Hitachi (JP); Kazuhiro Zama, Mito (JP); Kazuo Takahashi, Ninomiya (JP); Yusuke Miyazaki, Hitachinaka (JP); Shingo Tanaka, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 8 days.

(21) Appl. No.: 12/275,746

(22) Filed: Nov. 21, 2008

(65) Prior Publication Data

US 2009/0147246 A1 Jun. 11, 2009

Related U.S. Application Data

(63) Continuation of application No. 11/709,873, filed on Feb. 23, 2007, now abandoned.

(30) Foreign Application Priority Data

| Feb. 24, 2006 | (JP) | ............................. 2006-048124 |
| Feb. 24, 2006 | (JP) | ............................. 2006-048130 |
| Mar. 14, 2006 | (JP) | ............................. 2006-068476 |

(51) Int. Cl.
*G01N 21/00* (2006.01)
(52) U.S. Cl. ................................. 356/237.2; 356/237.1
(58) Field of Classification Search ... 356/237.1–237.6, 356/239.7–239.8; 250/559.01–559.49
See application file for complete search history.

(56) References Cited

U.S. PATENT DOCUMENTS

| 7,292,341 | B2 | 11/2007 | Brill et al. |
| 2004/0008341 | A1 | 1/2004 | Iizuka et al. |
| 2005/0270522 | A1* | 12/2005 | Miyakawa et al. ....... 356/237.2 |
| 2006/0044556 | A1 | 3/2006 | Kawano |

FOREIGN PATENT DOCUMENTS

| JP | 7-235579 | 9/1995 |
| JP | 2004-45111 | 2/2004 |
| JP | 2005-156537 | 6/2005 |

\* cited by examiner

*Primary Examiner*—Gregory J Toatley, Jr.
*Assistant Examiner*—Tri T Ton
(74) *Attorney, Agent, or Firm*—McDermott Will & Emery LLP

(57) ABSTRACT

A laser beam oscillated from a laser source is folded in its path by first and second plane mirrors and enters a beam expander. The surface of each plane mirror is deteriorated with illumination by the laser beam and the reflectance is reduced. To avoid a light quantity of the laser beam entering the beam expander from being reduced below a reference value, when the laser beam is illuminated over a certain time, a position on each of the first and second plane mirrors at which the laser beam is illuminated is changed by a structure for rotating and/or translating a reflecting surface of each plane mirror on a plane, which includes the plane mirror, while an optical axis is kept same. Thus, the useful life of each plane mirror can be prolonged without displacing the optical axis.

5 Claims, 14 Drawing Sheets

OPTICAL DEFECT INSPECTION APPARATUS

RELATED APPLICATIONS

This application is a Continuation of U.S. application Ser. No. 11/709,873, filed Feb. 23, 2007, now abandoned claiming priority of Japanese Application Nos. 2006-048124, filed Feb. 24, 2006; 2006-048130, filed Feb. 24, 2006; and 2006-068476, filed Mar. 14, 2006, the entire contents of each of which are hereby incorporated by reference.

BACKGROUND OF THE INVENTION

1. Field of the Invention

The present invention relates to an apparatus and a method for inspecting an object to be inspected (i.e., an inspection target). More particularly, the present invention is adapted for an optical defect inspection apparatus and method for inspecting foreign matters, defects, etc. on inspected objects in manufacturing processes of, e.g., semiconductor devices, flat panel displays, magnetic disks, and masks.

2. Description of the Related Art

The capability of detecting finer defects is demanded in an optical defect inspection apparatus for illuminating a light to an object to be inspected, such as a semiconductor device and a flat panel display, and measuring the light reflected or scattered from the object. To meet such a demand, using a light source with higher luminance is required and a laser beam is mainly used as the light source. One known inspection apparatus using the laser beam is disclosed in Patent Document 1 (JP,A 2005-156537). On the other hand, with an increase of needs for unified management of inspection conditions, stability and reproducibility of the inspection apparatus are also demanded in addition to higher detection sensitivity.

When a laser beam is employed as the light source, a thin beam with a high illumination density has to be used until reaching an ND (Neutral Density) filter, which is used to adjust the light quantity (intensity), due to the necessity of avoiding an increase in size of an ND filer mechanism. Also, from the viewpoint of ensuring flexibility in apparatus layout, the inspection apparatus is usually constructed such that a thin beam with a high illumination density is reflected several times within an apparatus housing by reflecting mirrors (plane mirrors). In such a case, when the laser beam is illuminated to the same position of the plane mirror for a long time, there occurs a problem in stability that the mirror surface in an illuminated area is deteriorated, the reflection is reduced, and the illumination intensity cannot be held at a required level.

If the reflectance is reduced, the plane mirror has to be replaced. After the replacement, a slight deviation of an optical axis is unavoidable. To compensate for such a deviation of the optical axis, Patent Document 2 (JP,A 2004-45111) discloses the provision of a mechanism for changing an angle of a plane mirror.

Further, in addition to the above-mentioned change of the illumination intensity due to deterioration of the plane mirror, dust generated from an actuator and a variation of the focal length caused by flexing of the inspected object become factors acting to reduce stability and reproducibility of the inspection apparatus. One example of actuators having a structure to cope with generation of dust is disclosed in Patent Document 3 (JP,A 7-235579).

SUMMARY OF THE INVENTION

For the purpose of avoiding intricate adjustment of the optical axis, the known apparatus is constructed such that the laser beam is illuminated to the same point on the plane mirror (reflecting mirror). However, replacing the plane mirror whenever its reflection is reduced causes a problem in point of cost efficiency. Also, changing the laser illuminated point on the plane mirror to avoid frequent replacement is not easy to practice in the known apparatus.

An object of the present invention is to prolong the useful life of a plane mirror (each of first and second plane mirrors) without displacing an optical axis itself, taking into account the above-described problem that when a laser beam is employed as the light source and a thin beam with a high illumination density is illuminated to the same position on each of the first and second plane mirrors for a long time, the surface of the plane mirror is deteriorated, the reflectance is reduced, and the light quantity cannot be held at a required level.

With a progress toward finer patterns of semiconductor devices, the presence of dust in manufacturing and inspection steps of the semiconductor devices, particularly, in steps of processing an object (wafer) to be inspected, gives a significant influence upon a yield of products. In a processing apparatus and an inspection apparatus used in the wafer processing steps, therefore, it is desired that no dust is generated from the apparatuses. The generation of dust causes deposition of foreign matters on the inspected object during transport and inspection thereof, and deteriorates reproducibility of the inspection apparatus. Among various dust sources, in particular, actuators used in various mechanisms and tending to easily generate powdery dust with sliding give rise to serious influences, and therefore they are desired to be kept from generating dust.

Besides the actuator disclosed in Patent Document 3, another known actuator for a linearly reciprocating device is shown in FIG. 14. The known actuator for the linearly reciprocating device of FIG. 14 has the problem that dust generated inside a cylinder 803 is discharged together with pressurized air leaking through a clearance between a piston rod 805 and a seal ring 807.

In order to avoid the above problem, a dust collection chamber 803C for collecting the pressurized air including generated dust is required to be disposed around the piston rod 805 and the seal ring 807. The provision of the dust collection chamber 803C significantly limits layout of a vacuum source 821 and a line 819, which are also arranged nearby for evacuation. There is hence a demand for a linearly reciprocating device which can suppress the generation of dust without needing the vacuum source and the line for evacuation.

Further, in a manufacturing process of a 300-mm wafer, the rear surface of the wafer is also finished to a mirror-smooth surface. However, deposited foreign matters and protrusive defects on the rear surface deteriorate flatness of the front surface and cause abnormal focusing of exposed light in the lithography step. Also, the foreign matters deposited on the rear surface may shift to the front surface and reduce a yield in some cases. For that reason, the function of detecting defects on the rear surface is demanded.

For inspecting the rear surface of an inspected object, it is required to hold the inspected object at the edge thereof and inspect the rear surface in a non-contact manner. However, because there are no contact portions to support the rear surface of the inspected object, a reduction may occur in flatness of the inspected object, or flexing of the inspected object itself may occur. Accordingly, the height of the front surface of the inspected object is deviated from the focal length of an optical system, thus deteriorating stability and reproducibility of the inspection apparatus, such as a reduction of sensitivity, a larger variation of sensitivity, and degradation in accuracy of coordinates set on the inspected object. Improvement of the flatness and compensation of the flexing have been practiced by a method of spraying gas with high cleanness to the rear surface of the inspected object and compensating for the flexing of the inspected object by the action of gas pressure. At a level of sensitivity having been required so far, such a method can hold a variation in the height of the front surface of the inspected object within the focal range of the optical system and can realize a measurement that satisfies the required levels of the sensitivity variation and the coordinate accuracy. With a trend toward higher sensitivity of the defect inspection apparatus, however, higher flatness of the inspected object is demanded.

Generally, the higher sensitivity, the shallower is the focal depth of the optical system. This means that, at the level of flatness which has been used so far, a local deviation of the focal position is caused on the front surface of the inspected object, thus resulting in a variation and reduction of sensitivity on the front surface of the inspected object, as well as degradation of the coordinate accuracy for the detected foreign matters. Further, the method of spraying gas to the rear surface of the inspected object and compensating for the flexing thereof has a limitation on flatness that can be realized. In addition, that method requires complicated control for spraying gas so as to be adapted for a variety of inspected objects which differ in film type, thickness, crystal azimuth, extent of warp, etc. To overcome those problems, a system capable of always compensating for the deviation of the focal position on the front surface of the inspected object is demanded.

To overcome the above problems and to achieve the above object, the present invention is featured in providing one or more mechanisms capable of moving a beam illuminated position on each of a first reflecting mirror and a second reflecting mirror, which reflect an illuminated laser beam, and changing a position of reflection on the reflecting mirror with one or both of rotation and translation of the reflecting mirror on a reflecting including the reflecting mirror while an optical axis itself is kept same, thereby allowing the use of a position on the reflecting mirror where the reflectance is not reduced. Also, those mechanisms can be realized with a manual, automatic or programmed way based on the illumination intensity measured before and behind the reflecting mirror.

One feature of the present invention resides in an optical defect inspection apparatus including a beam deflection mechanism comprising a laser source, a first reflecting mirror for reflecting a laser beam emitted from the laser source at a predetermined angle, and a second reflecting mirror for reflecting again the laser beam reflected by the first reflecting mirror and producing a laser beam which advances in a predetermined direction with respect to the laser beam emitted from the laser source, wherein the optical defect inspection apparatus further includes a reflecting mirror moving mechanism for moving at least one of the first reflecting mirror and the second reflecting mirror while an angle of incidence and an angle of reflection of the laser beam are maintained same.

Another feature of the present invention resides in that at least one of the predetermined angle at which the laser beam is reflected by the first reflecting mirror and the predetermined angle at which the laser beam is reflected by the second reflecting mirror is substantially 90 degrees, and the reflecting mirror moving mechanism moves at least one of the first reflecting mirror and the second reflecting mirror such that a reflecting surface of the moved reflecting mirror is kept in a substantially parallel condition.

Still another feature of the present invention resides in that at least one of the predetermined angle at which the laser beam is reflected by the first reflecting mirror and the predetermined angle at which the laser beam is reflected by the second reflecting mirror is substantially 90 degrees, and the reflecting mirror moving mechanism rotates at least one of the first reflecting mirror and the second reflecting mirror such that a reflecting surface of the moved reflecting mirror is rotated substantially parallel.

Still another feature of the present invention resides in that the reflecting mirror moving mechanism includes a mechanism for linearly moving at least one of the first reflecting mirror and the second reflecting mirror such that the reflecting surface of the moved reflecting mirror is kept in a substantially parallel condition.

Still another feature of the present invention resides in that the optical defect inspection apparatus further includes a light quantity measuring mechanism for measuring a light quantity of the laser beam reflected by at least one of the first reflecting mirror and the second reflecting mirror.

Still another feature of the present invention resides in a defect inspection apparatus including a linearly moving device which comprises a cylinder having a piston chamber and a dust collection chamber which are formed therein adjacent to each other, a piston disposed in the piston chamber to be able to slide and reciprocate therein, a piston rod fixed to the piston and extended to the outside of the cylinder after penetrating through an adjacent wall and the cylinder, and a biasing spring disposed in the piston chamber and acting to press the piston in a direction toward the dust collection chamber, wherein the piston is operated such that the piston is moved against the biasing spring by pressurized air supplied to one side of the piston chamber divided by the piston and is pushed back by a resilient force of the biasing spring, and gas in the dust collection chamber is moved toward the other side of the piston chamber in which pressure is lowered with an increase of a space volume corresponding to the pushed-back movement of the piston.

Still another feature of the present invention resides in that the linearly moving device employs, as the biasing spring, a compression-type biasing spring and the compression-type biasing spring is built in the other side of the piston chamber.

Still another feature of the present invention resides in a defect inspection apparatus including a linearly moving device which comprises a cylinder having a piston chamber and a dust collection chamber which are formed therein adjacent to each other, a piston disposed in the piston chamber to be able to slide and reciprocate therein, a piston rod fixed to the piston and extended to the outside of the cylinder after penetrating through an adjacent wall within the cylinder and an outer wall of the dust collection chamber, a biasing spring disposed in one side of the piston chamber divided by the piston and acting to press the piston in a direction toward the dust collection chamber, a pressurized air pump for supplying pressurized air to the other side of the piston chamber in which the biasing spring is not disposed (i.e., a biasing spring not-built-in chamber), a pressurized air tube allowing passage of the pressurized air therethrough, a flow switching solenoid valve disposed in the pressurized air tube, a discharge tube communicating with the one side of the piston chamber in which the biasing spring is disposed (i.e., a biasing spring built-in chamber), a filter disposed in the discharge tube and filtering out dust in discharged gas, and a dust-collection-chamber discharge tube for communicating the dust collection chamber with the aforesaid discharge tube or the biasing spring built-in chamber, wherein a check valve for the dust-collection-chamber discharge tube is disposed in the dust-collection-chamber discharge tube to check a gas flow directing from the biasing spring built-in chamber toward the dust collection chamber, and a check valve for the discharge tube is disposed in the discharge tube to check a gas flow directing from the filter toward the biasing spring built-in chamber.

Still another feature of the present invention resides in that, in any of the above-described defect inspection apparatuses each including the linearly moving device, the piston operates a wafer clamping mechanism or a wafer handling/carrying mechanism.

Still another feature of the present invention resides in that, in any of the above-described defect inspection apparatuses each including the linearly moving device, the pressurized air pump and the flow switching solenoid valve are disposed in a down flow area which is not subjected to dust cleaning, while other components than the pressurized air pump and the flow switching solenoid valve are disposed in a clean flow area which is subjected to dust cleaning.

Still another feature of the present invention resides in a defect inspection apparatus comprising a light illuminating unit for illuminating a light to an object to be inspected, a first light detecting unit of an optical system for detecting a light scattered from the inspected object, an inspected object moving unit for moving the inspected object such that a position on the inspected object illuminated by the light from the light illuminating unit is changed, an inspected object holding unit for holding the inspected object, and a focal position aligning unit for detecting the light illuminated from the light illuminating unit and reflected by the inspected object, obtaining height information of a surface of the inspected object, and aligning a focal position of the first light detecting unit of the optical system based on the obtained information.

Still another feature of the present invention resides in that, in any of the above-described defect inspection apparatuses, the focal position aligning unit includes a second light detecting unit for detecting the light illuminated from the light illuminating unit and reflected by the inspected object, and a control system for executing control based on height information, which is detected by the second light detecting unit and is fed back, such that the focal position and the surface of the inspected object are held at the same height.

Still another feature of the present invention resides in, in any of the above-described defect inspection apparatuses, further comprising a light quantity optimizing unit for optimizing a quantity of the reflected light from the inspected object by an optical element, etc.

Still another feature of the present invention resides in that, in any of the above-described defect inspection apparatuses, the inspected object is supported at an outer peripheral edge thereof by the inspected object holding unit, thereby enabling the inspected object to be inspected while a rear surface of the inspected object is kept in a non-contact state.

Still another feature of the present invention resides in that, in any of the above-described defect inspection apparatuses, the focal position is aligned by combined control of an operation of vertically moving the inspected object holding unit and an operation of spraying the gas toward the rear surface thereof.

Still another feature of the present invention resides in that, in any of the above-described defect inspection apparatuses, the inspected object is two-dimensionally moved by moving the inspected object in one direction while the inspected object is rotated.

According to the one feature of the present invention, since the reflecting mirror is provided with the translation mechanism and the rotation mechanism both causing no displacements of the optical axis, frequency of part replacement can be reduced and alignment of the optical axis of the reflecting mirror can be dispensed with.

DESCRIPTION OF THE PREFERRED EMBODIMENTS

First Embodiment

A first embodiment of the present invention will be first described in detail below with reference to the drawings. A defect inspection apparatus of the first embodiment is intended to suppress variations of conditions, such as a reduction of light quantity (intensity) caused by deterioration of a plane mirror (reflecting mirror), with the provision of a translation mechanism and/or a rotation mechanism, which does not displace an optical axis of the plane mirror, in an optical system.

Figure 1:
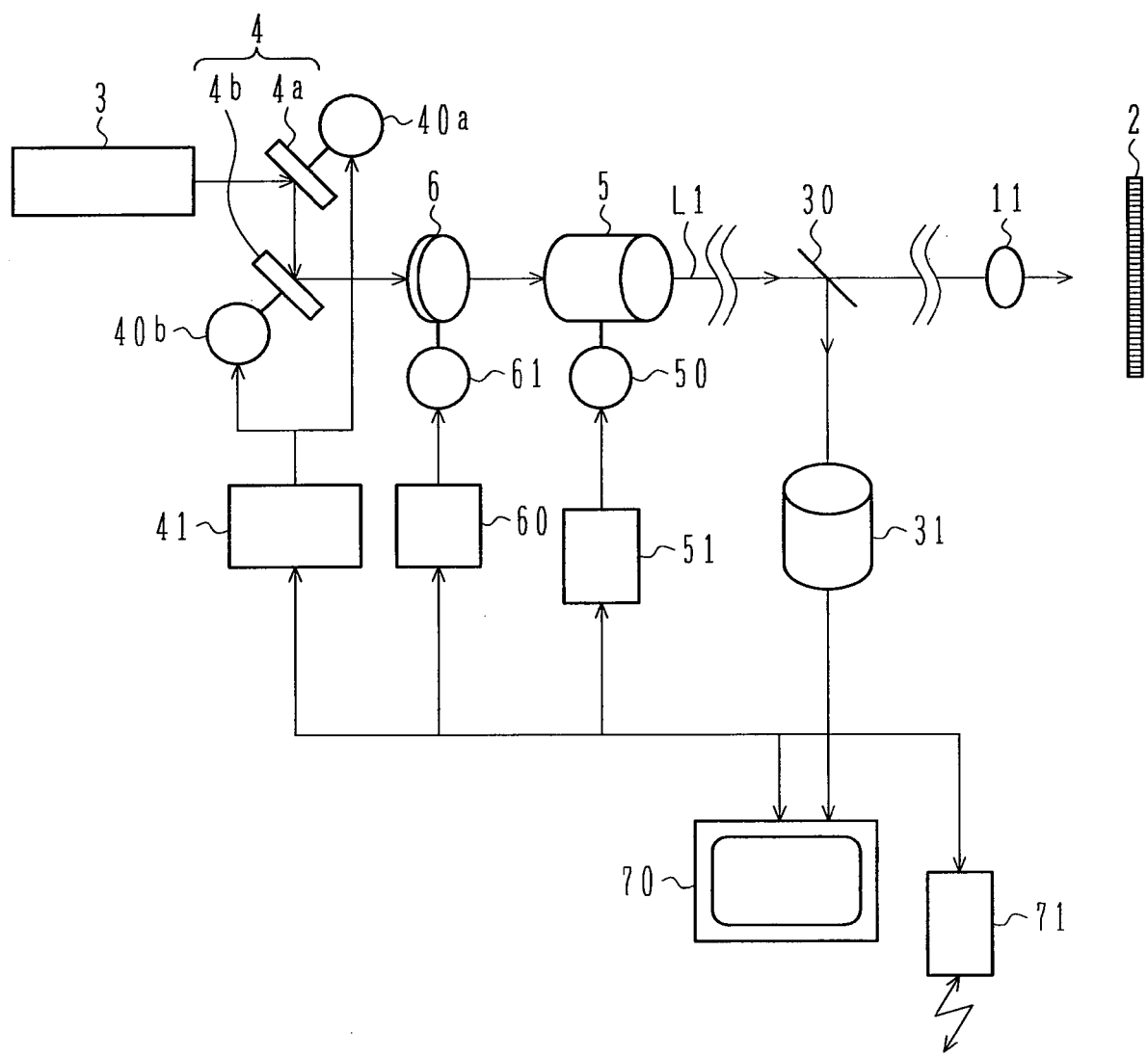
FIG. 1 is a diagram showing the construction of an illumination optical system according to a first embodiment of the present invention.

FIG. 1 schematically shows the construction of an illumination optical system according to the first embodiment of the present invention. The illumination optical system primarily comprises a laser source 3 for emitting an illumination light, e.g., a visible or ultraviolet laser beam, a beam deflection mechanism 4 made up of a plurality of pane mirrors, such as a first plane mirror (reflecting mirror) 4a and a second plane mirror (reflecting mirror) 4b, for deflecting the direction of advance of an oscillated later beam L1, an ND filter 6 for adjusting a light quantity, an expander 5 for adjusting a beam diameter, a beam splitter 30 for splitting the laser beam L1, an object lens 11 for shaping the beam shape of the laser beam L1 advancing along one of split paths and illuminating it to the surface of an object 2 to be inspected, a beam profile observation camera 31 for picking up an image of the laser beam L1 advancing along the other split path, and a host computer 71 for controlling the entirety of the inspection apparatus.

The first plane mirror 4a is arranged to reflect the laser beam L1 at a predetermined angle. The second plane mirror 4b is arranged to reflect again the laser beam L1, which has been reflected by the first plane mirror 4a, at a predetermined angle so that the laser beam L1 advances in a predetermined direction with respect to the direction in which the laser beam L1 was emitted from the laser source 3. In this first embodiment, the laser beam L1 is reflected at an angle of substantially 90° two times. Such an uneven parallel arrangement of the laser source 3 and the optical elements is advantageous in improving maintainability, e.g., adjustment of the optical system and replacement of the laser source 3 after expiration of its life.

Those two angles of reflection of the laser beam L1 are not limited to 90° or thereabout. It is just enough that at least one of the two angles of reflection of the laser beam L1 is substantially 90°. When the angle of reflection of the laser beam L1 is other than 90°, a plurality of plane mirrors may be arranged such that the illuminated laser beam L1 and the reflected laser beam L1 are alternately reflected by and illuminated to the plane mirrors. The angles of the plane mirrors may be set equal to each other for parallel arrangement, or the angle of one or more intermediate plane mirrors may be changed so long as the laser beam L1 can be bent to advance in the predetermined direction.

The laser beam L1 oscillated from the laser source 3 is reflected by the first plane mirror 4a substantially at 90° to advance downward. Then, the laser beam L1 is reflected again by the second plane mirror 4b substantially at 90° to advance horizontally. The laser beam L1 thus folded in its path enters the ND filter 6 in which the light quantity is adjusted, and then enters the beam expander 5 in which the beam diameter is adjusted.

The first plane mirror 4a and the second plane mirror 4b are controlled by a control unit 41 of plane mirror moving mechanisms such that illuminated positions on those mirrors can be moved while the angles of incidence and the angles of reflection are kept same by plane mirror moving mechanisms 40a and 40b corresponding to the first and second plane mirror 4a, 4b, respectively. In other words, the positions on the first plane mirror 4a and the second plane mirror 4b where the laser beam L1 is illuminated can be changed without displacing an optical axis. The adjustment of the light quantity in the ND filter 6 is controlled through an ND filter moving mechanism 61 by a control unit 60 of the ND filter moving mechanism, and the adjustment of the beam diameter in the beam expander 5 is controlled through a beam expander adjusting mechanism 50 by a control unit 51 of the beam expander adjusting mechanism.

After passing through various optical elements for control of the beam status such as the state of polarization and the beam diameter, the laser beam L1 is split into two paths by the beam splitter 30. The laser beam L1 advancing along one of the split paths passes through several optical elements for adjustment of the beam shape and status, and is illuminated to the surface of the inspected object 2 through the object lens 11. An image of the laser beam L1 advancing along the other split path is picked up by the beam profile observation camera 31, whereby the position of the laser beam L1 and the illuminance distribution within the laser beam L1 are displayed on a monitor 70. The host computer 71 transmits and receives data among the control unit 41 of the plane mirror moving mechanisms, the control unit 60 of the ND filter moving mechanism, and the control unit 51 of the beam expander adjusting mechanism in accordance with instructions entered from an input device (not shown), such as a keyboard or a mouse, and it drives the plane mirror moving mechanisms 40a and 40b, the ND filter moving mechanism 61, and the beam expander adjusting mechanism 50 which correspond to the those control units, thereby controlling the beam status of the laser beam L1. Further, the host computer 71 executes overall control of the defect inspection apparatus including, e.g., not only display of various setting conditions, the inspection results, the operating state of the inspection apparatus, etc. on the monitor 70, but also outputting of such information to an output device (not shown).

Figure 2:
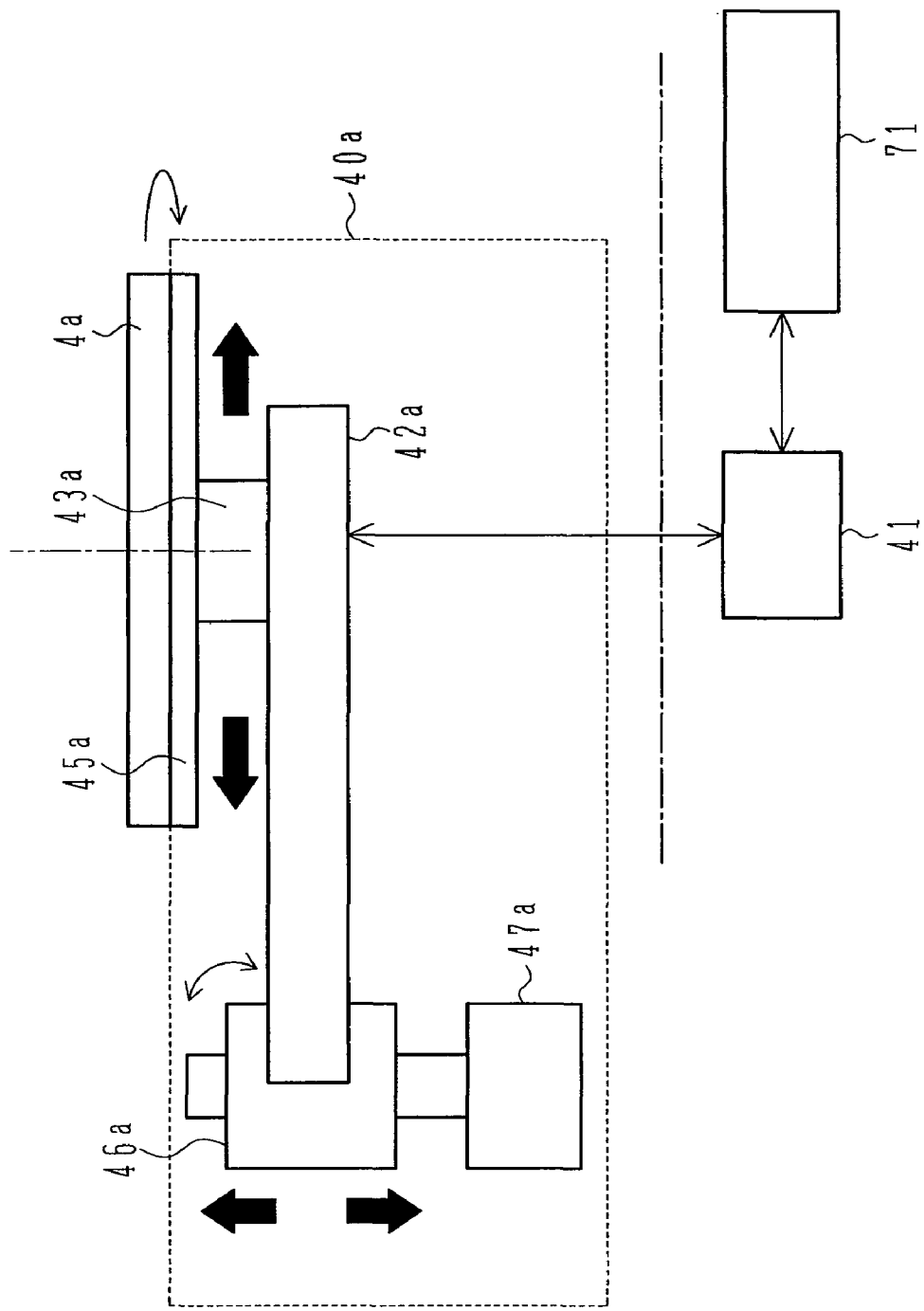
FIG. 2 is a schematic view showing the construction of a plane mirror moving mechanism according to the first embodiment of the present invention.

FIG. 2 schematically shows the construction of the plane mirror moving mechanism 40a. Since the plane mirror moving mechanism 40b also has the same construction, the plane mirror moving mechanism 40a is described here as a typical example.

The plane mirror moving mechanism 40a comprises a stage 45a for supporting the plane mirror 4a in a fixed state, an extension/retraction driving mechanism (linear driving mechanism) 42a for moving the plane mirror 4a while keeping the reflecting surface of the plane mirror 4a in a substantially parallel condition, a rotation driving mechanism 43a for rotating the plane mirror 4a while keeping the reflecting surface of the plane mirror 4a in a substantially parallel condition, an angle correcting mechanism 46a for correcting the angle of the reflecting surface, and a distance correcting mechanism 47a for correcting the distance between the laser source 3 and the plane mirror 4a or the distance between the plane mirrors 4a and 4b.

Position sensors (not shown) are disposed respectively in association with the extension/retraction driving mechanism 42a, the rotation driving mechanism 43a, the angle correcting mechanism 46a, and the distance correcting mechanism 47a.

The control unit 41 of the plane mirror moving mechanisms calculates coordinate values of the position of the plane mirror 4a based on a signal from the associated position sensor (not shown), and controls the plane mirror 4a to be moved to the position coordinates, which are instructed from the host computer 71, through the extension/retraction driving mechanism 42a and the rotation driving mechanism 43a. The calculation of the position coordinates may be executed by the host computer 71.

The position coordinates of the plane mirror 4a fixed on the stage 45a are changed with rotation by the rotation driving mechanism 43a and with movement in the direction of one axis by the extension/retraction driving mechanism 42a, for example, on condition that a point for start of the illumination by the laser beam L1 is set to substantially the center of the plane mirror 4a. Accordingly, the position illuminated by the laser beam L1 is relatively moved on the reflecting surface of the plane mirror 4a along a spiral, volute or circular locus while maintaining the state of the optical axis, whereby a usable area of the reflecting surface is enlarged. The enlargement of the usable area is controlled by the pitch at which the plane mirror 4a is moved by the extension/retraction driving mechanism 42a, and the useful life of the plane mirror 4a is drastically prolonged. Also, with the provision of the position sensor, the coordinates of the illuminated position can be correctly measured. It is therefore possible to restore the past inspection state and to search for and select a satisfactory position within the reflecting surface of the plane mirror 4a. With the provision of the angle correcting mechanism 46a and the distance correcting mechanism 47a, it is further possible to absorb variations in mounting accuracy, thickness, parallelism, and surface flexure depending on individual plane mirrors 4a, to facilitate (automate) the correction of the optical axis at the time of part replacement, and to keep the optical axis in a stable state.

While this first embodiment uses the plane mirror moving mechanism 40a capable of ensuring high efficiency in use of the plane mirror 4a and holding the optical axis with high accuracy, only a moving mechanism for moving the plane mirror 4a while keeping the reflecting surface of the plane mirror 4a in a substantially parallel condition may also be used instead. Alternatively, only a moving mechanism for rotating the plane mirror 4a while keeping the reflecting surface of the plane mirror 4a in a substantially parallel condition may be used instead. Those modifications are inferior in efficiency of use to the first embodiment, but they are advantageous in that the size and the production cost of the plane mirror moving mechanism 40a can be reduced. Further, although the position sensors associated with the extension/retraction driving mechanism 42a and the rotation driving mechanism 43a are necessary to restore the past inspection conditions and to select a satisfactory position on the reflecting surface of the plane mirror 4a, they are not essential from the viewpoint of enlarging the usable area of the reflecting surface. In other words, a simple moving mechanism known to those skilled in the art and made of gears, a belt, etc. may also be used to move the illuminated position in units of a predetermined distance.

The surface of each of the first plane mirror 4a and the second plane mirror 4b is deteriorated and its reflectance is reduced when the mirror surface is exposed to the laser beam L1 for a long time. In order to prevent the light quantity of the laser beam entering the beam expander 5 from being reduced to a reference value or below due to the reduction of the mirror reflectance, the position on each of the first plane mirror 4a and the second plane mirror 4b where the laser beam L1 emitted from the laser source 3 is illuminated is changed by driving the plane mirror moving mechanism 40a and the plane mirror moving mechanism 40b without changing the optical axis itself, when the irradiation time of the laser beam L1 exceeds a certain period, for example. As an alternative, the host computer 71 may control the control unit 41 of the plane mirror moving mechanisms to change the illuminated position, while monitoring change of the light quantity reflected by the plane mirror, at the time when the monitored light quantity is reduced to a preset threshold or below.

Thus, by employing the structure capable of rotating the specular surface of each of the plane mirrors in the beam deflection mechanism 4, or the structure capable of translating the specular surface, or both of those structures, replacement frequency of the plane mirror can be drastically reduced and the adjustment of the optical axis can be dispensed with. Further, it is possible to suppress mixing of dust into the optical system, which may be caused by the part replacement, and to hold down an increase in amount of foreign matters generated from the optical system.

Figure 3:
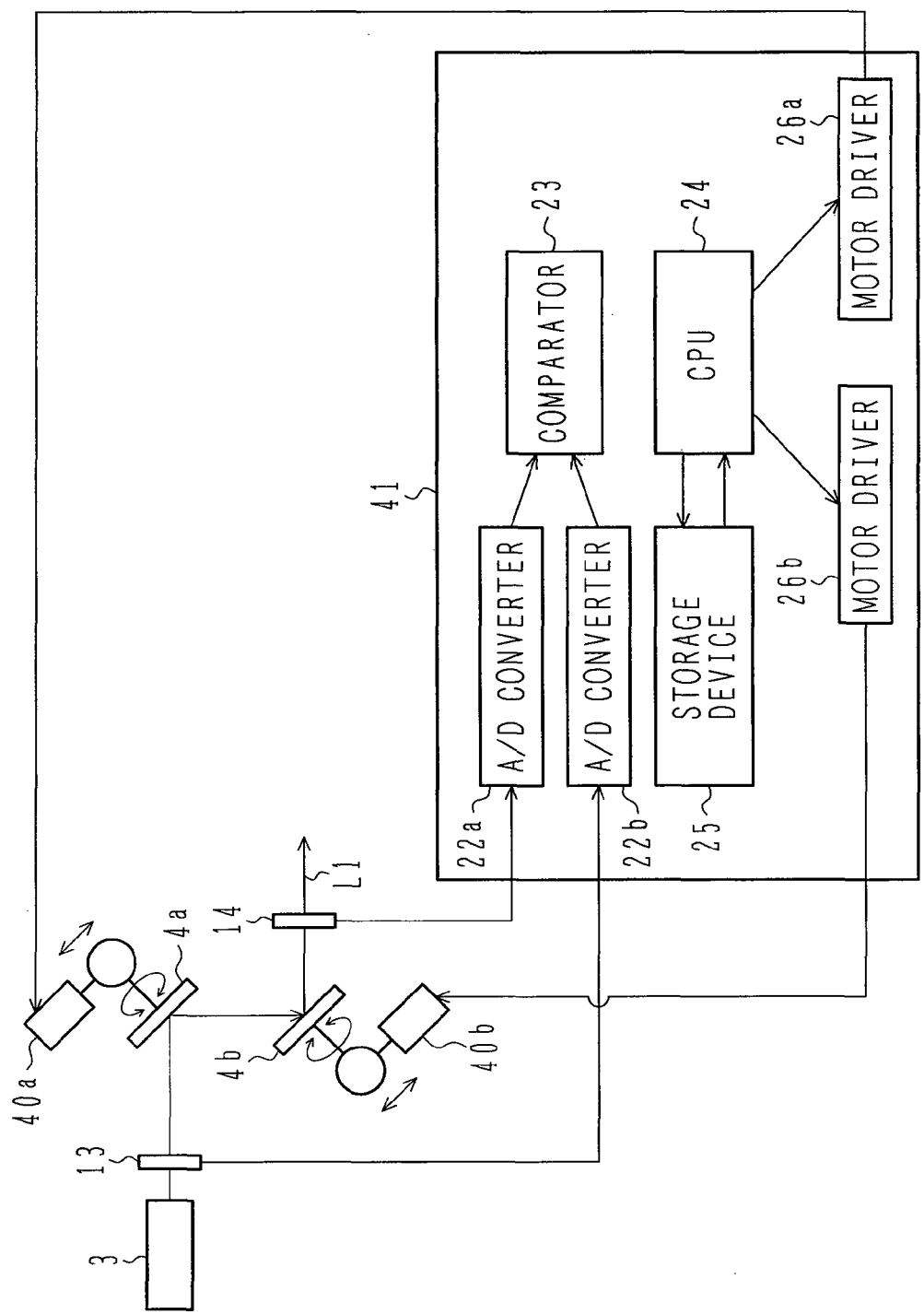
FIG. 3 is a diagram for explaining one practical operation of the plane mirror moving mechanism and a control unit according to the first embodiment of the present invention.

FIG. 3 shows one practical example of a process for controlling the plane mirror moving mechanism. A first light quantity monitor 13 (i.e., first light quantity measuring means) capable of measuring a light quantity is arranged between the laser source 3 and the first plane mirror 4a which can be rotated and/or translated without changing the optical axis. Also, a second light quantity monitor 14 (i.e., second light quantity measuring means) capable of measuring a quantity of the reflected light is arranged downstream of the second plane mirror 4b which can be rotated and/or translated without changing the optical axis. While this first embodiment is designed to measure a rate of deterioration resulting from both the surfaces of the first plane mirror 4a and the second plane mirror 4b, the quality of the reflected light may be measured for at least one of the two plane mirrors because the deterioration of the mirror surface is progressed substantially at the same rate. A similar function can also be obtained with another example in which the second light quantity measuring means is arranged between the first plane mirror 4a and the second plane mirror 4b. Further, if the light quantity is not changed with the movement of the illuminated position, this can be determined as indicating deterioration of the laser beam 3. Therefore, the light quantity measuring means may be constituted only by the second light quantity monitor 14 to measure the sum of deterioration of the laser source 3 and deteriorations of the first plane mirror 4a and the second plane mirror 4b. The plurality of light quantity measuring mechanisms, i.e., the first light quantity monitor 13 and the second light quantity monitor 14, are movable by a driving mechanism (not shown) corresponding to the first light quantity monitor and a driving mechanism (not shown) corresponding to the second light quantity monitor, respectively, such that both the monitors are moved to come into the optical axis only when the light quantity is measured, and that they are moved away from the optical axis when defects of the inspected object 2 are inspected.

The initial light quantity of the laser beam L1 oscillated from the laser source 3 is measured by the first light quantity monitor 13, and an electric signal (analog signal) from the monitor 13 is inputted to a first A/D converter 22a. The light quantity of the laser beam L1 having attenuated through the reflections by the first plane mirror 4a and the second plane mirror 4b is measured by the second light quantity monitor 14, and an electric signal (analog signal) from the monitor 14 is inputted to a second A/D converter 22b. The respective light quantities of the laser beam L1 measured by the first light quantity monitor 13 and the second light quantity monitor 14 are displayed on the monitor 70. Thus, it is possible to confirm not only the attenuation of the light quantity caused by the beam deflection mechanism 4, but also the deteriorated state of the laser source 3.

The analog signals inputted to the first A/D converter 22a and the second A/D converter 22b are both converted to digital signals which are inputted to a comparator 23. Based on the signal from the first A/D converter 22a, which represents the initial light quantity of the laser beam L1, and the signal from the second A/D converter 22b, which represents the light quantity of the laser beam L1 having attenuated through the beam deflection mechanism 4, the comparator 23 calculates the deterioration rate of both the first plane mirror 4a and the second plane mirror 4b and then transmits the calculated data to a CPU 24. The transmitted deterioration rate is displayed on the monitor 70 via the CPU 24.

A storage device 25 previously stores a threshold which is used as a reference for comparison of the deterioration rate and is entered through the input device (not shown). The CPU 24 compares the threshold with the deterioration rate which has been calculated by the comparator 23. At the time when the deterioration rate exceeds the threshold, an alarm for prompting the operator to move the illuminated position on each of the first plane mirror 4a and the second plane mirror 4b is displayed on the monitor 70 (i.e., plane-mirror alarm display means). Also, when the deterioration rate of the laser source 3 exceeds a predetermined value, an alarm for prompting the operator to replace the laser source 3 is likewise displayed on the monitor 70 (i.e., laser-source alarm display means).

For the measurement of the first light quantity monitor 13 and the second light quantity monitor 14 arranged as described above, a select function box is displayed on a display screen so that the operator can selectively start the measurement before the start of alignment or at the start of alignment.

The measurement of the first light quantity monitor 13 and the second light quantity monitor 14 arranged as described above can be started by clicking a button or an icon displayed on a maintenance screen.

The above-described alarm is displayed on the monitor 70 in the form of a dialog after the measurement, or is continuously displayed on a part of the screen until the plane mirror is moved, thus prompting the operator to move the relevant plane mirror.

In addition, an expiration date is also displayed as a guide for the remaining useful life.

When the plane mirror 4a or 4b is moved, the operator optionally sets the distance through which the plane mirror is to be moved.

When the plane mirror 4a or 4b is moved, the moving mechanism is operated to move the plane mirror at intervals of a pitch set as one of the parameters.

When the plane mirror 4a or 4b is moved, it is moved so as to provide an optimum light quantity in an automatic manner.

Figure 4:
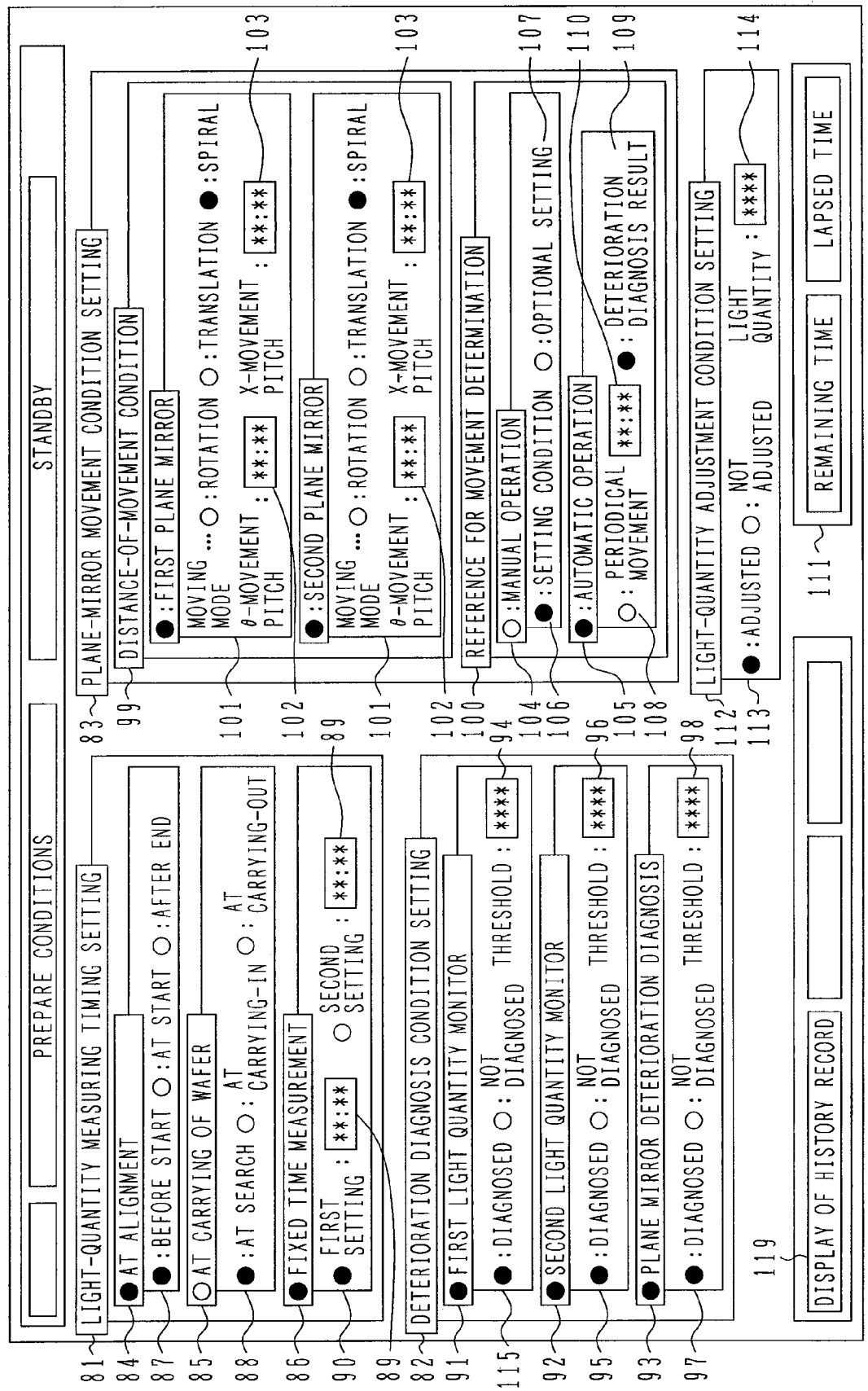
FIG. 4 illustrates a setting screen which is used to set deterioration diagnosis conditions for a plane mirror in the first embodiment of the present invention.

FIG. 4 shows one example of a setting screen used in this first embodiment. A diagnosis condition setting means (function) 80 is incorporated in the setting screen displayed for maintenance on the monitor 70. A screen indicating the diagnosis condition setting means 80 can be displayed, though not limited to particular one, by clicking a button or an icon prepared on a main screen. The diagnosis condition setting means 80 includes the functions executed by a measurement timing setting means 81 for setting the timing at which the light quantity is to be measured, a deterioration diagnosis condition setting means 82 for setting whether diagnosis is to be made or not and a reference for the deterioration determination, a movement condition setting means 83 for setting conditions for moving the first plane mirror 4a and the second plane mirror 4b, and a light-quantity adjustment condition setting means 112 for setting whether the light quantity of the laser beam L1 is to be adjusted or not when the plane mirror is moved.

The measurement timing setting means 81 includes the functions executed by an at-alignment measurement instructing means 84 for instructing the measurement to be executed at the time of alignment of the inspected object 2, an at-carrying measurement instructing means 85 for instructing the measurement to be executed at the time of carrying the inspected object 2 (wafer), and a fixed-time measurement instructing means 86 for instructing the measurement to be executed at the fixed time. The at-alignment measurement instructing means 84 includes the functions executed by an alignment step selecting means 87 for selecting in which one of steps the measurement is to be started, i.e., before the start, or at the start, or after the end of the alignment. The at-carrying measurement instructing means 85 includes the functions executed by a carrying step selecting means 88 for selecting in which one of steps the measurement is to be executed, i.e., at the time of searching the inspected object 2 in a cassette or a hoop, or at the time of carrying in the inspected object 2, or at the time of carrying out it. The fixed-time measurement instructing means 86 includes the functions executed by a time selecting means 90 having one or more time entry spaces 89 in each of which the time of starting the measurement is entered, and enabling one or more measurement start times to be selectively set. The measurement time can be entered into the space 89 through an input device (not shown), such as a keyboard or a mouse. Thus, the timing of executing the measurement can be selected as one or more from among the at-alignment measurement, the at-carrying measurement, and the fixed-time measurement.

The deterioration diagnosis condition setting means 82 includes the functions executed by a first light quantity monitor setting means 91, a second light quantity monitor setting means 92, and a deterioration (diagnosis) reference setting means 93. The first light quantity monitor setting means 91 includes the functions executed by a first light quantity measurement instructing means 115 for instructing whether the light quantity measurement by the first light quantity monitor 13 is to be made or not, and it has a first threshold entry space 94 in which a first threshold for the liquid quantity is entered. When the light quantity of the laser beam L1 does not satisfy the first threshold, an alarm indicating the deterioration of the laser source 3 and a message for prompting replacement thereof are displayed on the monitor 70. Similarly, the second light quantity monitor setting means 92 includes the functions executed by a second light quantity measurement instructing means 95 and has a second threshold entry space 96. When the deterioration reference setting means 93 is not used, the deterioration diagnosis of the first plane mirror 4a and the second plane mirror 4b may be performed based on a value of the light quantity measured by the second light quantity monitor 14 and the second threshold. The deterioration reference setting means 93 includes the functions executed by a deterioration diagnosis instructing means 97 for instructing whether the deterioration diagnosis of the first plane mirror 4a and the second plane mirror 4b is to be performed or not, and it has a third threshold entry space 98 in which a reference value for the deterioration determination is entered. When the deterioration rate calculated by the comparator 23 does not satisfy the third threshold, an alarm indicating the deterioration of the first plane mirror 4a and the second plane mirror 4b and a message for prompting change of the illustrated position are displayed on the monitor 70.

The movement condition setting means 83 includes the functions executed by a distance-of-movement setting means 99 for setting the distances through which the first plane mirror 4a and the second plane mirror 4b are to be moved, and a determination reference setting means 100 for setting a reference for the determination on the mirror movement. The distance-of-movement setting means 99 includes the functions executed by a moving mode instructing means 101 for instructing a moving mode of the first plane mirror 4a, and an angle-of-movement instructing means 102 and a distance-of-movement instructing means 103 for instructing pitches of the movement in the rotating direction and the linear direction, respectively. The moving mode can be selected from three modes, i.e., rotation, translation, and combination of rotation and translation (spiral movement). The first plane mirror 4a is driven to move in accordance with the pitches instructed by the angle-of-movement instructing means 102 and the distance-of-movement instructing means 103. Movement conditions for the second plane mirror 4b are also set in a similar manner. The determination reference setting means 100 includes the functions executed by a manual operation instructing means 104 and an automatic operation instructing means 105. The manual operation instructing means 104 enables the operator to select one of two modes provided by a setting condition selecting means 106 for moving the first plane mirror 4a and the second plane mirror 4b in accordance with the conditions instructed by the distance-of-movement setting means 99, and by an optional condition selecting means 107 for moving the first plane mirror 4a and the second plane mirror 4b in accordance with an instruction from the operator. When the setting condition selecting means 106 is selected, a movement request/cancel screen is displayed upon the alarm prompting the change of the illuminated position being displayed on the monitor 70. Then, the first plane mirror 4a and the second plane mirror 4b are moved by clicking a request (OK) button on the confirmation screen. When the optional condition selecting means 107 is selected, a setting screen similar to that for the distance-of-movement setting means 99 is displayed and the first plane mirror 4a and the second plane mirror 4b are moved by entering data of the pitch for each movement and clicking a button which is prepared on the displayed screen and which serves as a movement instruction means. The automatic operation instructing means 105 enables selection of one of two modes provided by a periodic movement instructing means 108 for automatically moving the first plane mirror 4a and the second plane mirror 4b in accordance with an instructed period, and by a deterioration diagnosis result instructing means 109 for moving the first plane mirror 4a and the second plane mirror 4b in accordance with the result of the deterioration diagnosis. In any of the two automatic operation modes, the first plane mirror 4a and the second plane mirror 4b are moved in accordance with the conditions set by the distance-of-movement setting means 99. The periodic movement instructing means 108 includes the function executed by a period instructing means 110 for instructing a period after the lapse of which the first plane mirror 4a and the second plane mirror 4b are to be moved. In this first embodiment, such a period is defined as an actual irradiation time of the laser beam L1 accumulated from the preceding mirror movement. That period is not limited to a particular one, and it may be given as the lapsed time from the preceding mirror movement or set based on a calendar or a schedule, such as the date of periodical diagnosis of the inspection apparatus, the maintenance date, or the time several hours before the start of the inspection. When the actual irradiation time accumulated per inspection exceeds the period instructed by the period instructing means 110, the first plane mirror 4a and the second plane mirror 4b are moved. The accumulated actual irradiation time (lapsed time) and the remaining time until the next movement are always displayed by the function of a period display means 111 disposed on a part of the monitor 70. When the mode for moving the plane mirrors based on the diagnosis result is selected by the deterioration diagnosis result instructing means 109, whether to move the plane mirrors or not is determined by the CPU 24 based on the setting conditions set by the measurement timing setting means 81 and the deterioration diagnosis condition setting means 82, and the plane mirrors are moved in accordance with the conditions set by the distance-of-movement setting means 99.

The light-quantity adjustment condition setting means 112 includes the functions executed by an adjustment request/cancel instructing means 113 for instructing whether the light quantity of the laser beam L1 is to be adjusted or not, and by an adjusted light-quantity instructing means 114 for instructing a value of the light quantity to be adjusted. The adjustment request/cancel instructing means 113 enables the operator to select one of two options, i.e., whether the light quantity of the laser beam L1 is to be adjusted or not after moving the first plane mirror 4a and the second plane mirror 4b. The adjusted light-quantity instructing means 114 is constituted as an entry space in which a target value of the light quantity to be adjusted can be set through the input device.

For example, when the adjustment of the light quantity is selected, the output of the laser source 3 is controlled so as to provide the setting value of the adjusted light-quantity instructing means 114 while measuring the light quantity of the laser beam L1 by the second light quantity monitor 14. At the time when the CPU 24 determines that the light quantity of the laser beam L1 is substantially equal to the setting value, the light quantity adjustment process is brought to an end and the output value of the laser source 3 is held fixed.

Figure 5:
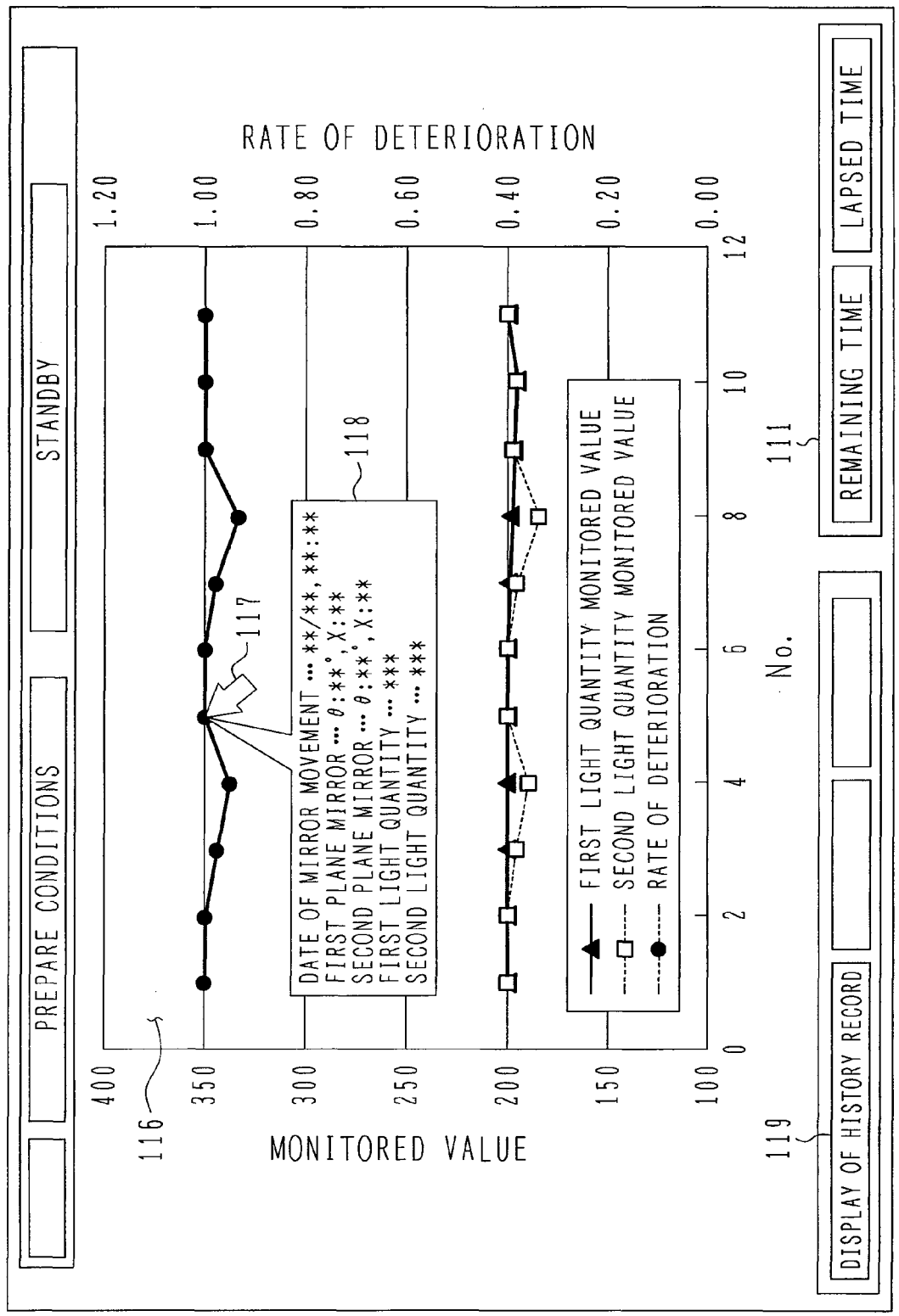
FIG. 5 illustrates a setting screen which displays a history record in the first embodiment of the present invention.

FIG. 5 shows a history record representing the past state of the light quantity and the driven state of each plane mirror moving mechanism 40a (40b). The history record regarding the values of the light quantity measured by the first light quantity monitor 13 and the second light quantity monitor 14, the deterioration rate calculated by the comparator 23, the dates when the first plane mirror 4a and the second plane mirror 4b were moved, the coordinates of the illuminated positions on the plane mirrors, etc. are stored in the storage device 25 via the CPU 24. A history record management chart 116 is displayed by clicking a button representing the function of a history record display means 119, which is prepared in the screen displayed on the monitor 70, through the input device. The history record of the measured results of the light quantity and the driven state of each plane mirror moving mechanism 40a (40b) is displayed in a comment column 118 by selecting a plotted mark with a pointer 117. By clicking the comment column 118, the state of the optical system is restored to the state at the time corresponding to the selected mark. Changes of the optical system can be more accurately confirmed by performing the periodical measurement in accordance with an instruction from the periodical measurement instructing means 86.

While the entry means and the display means for the setting values are constituted, by way of example, in the form of spaces and buttons in the first embodiment, other suitable signal input/transmission means and display means are also usable, e.g., icons and a keyboard, so long as they can enter, transmit and display signals.

Second Embodiment

A second embodiment of the present invention will be described in detail below with reference to the drawings. This second embodiment represents the case where the present invention is applied to a surface inspection apparatus. The surface inspection apparatus has the functions of inspecting not only the front surface of an object to be inspected, but also the rear surface thereof. The surface inspection apparatus includes the plane mirror moving mechanisms, the light quantity measuring means, the control means for them, and the diagnosis condition setting means, which are all described above in connection with the first embodiment, but an optical system in the second embodiment differs from that in the first embodiment to some extent.

Figure 6:
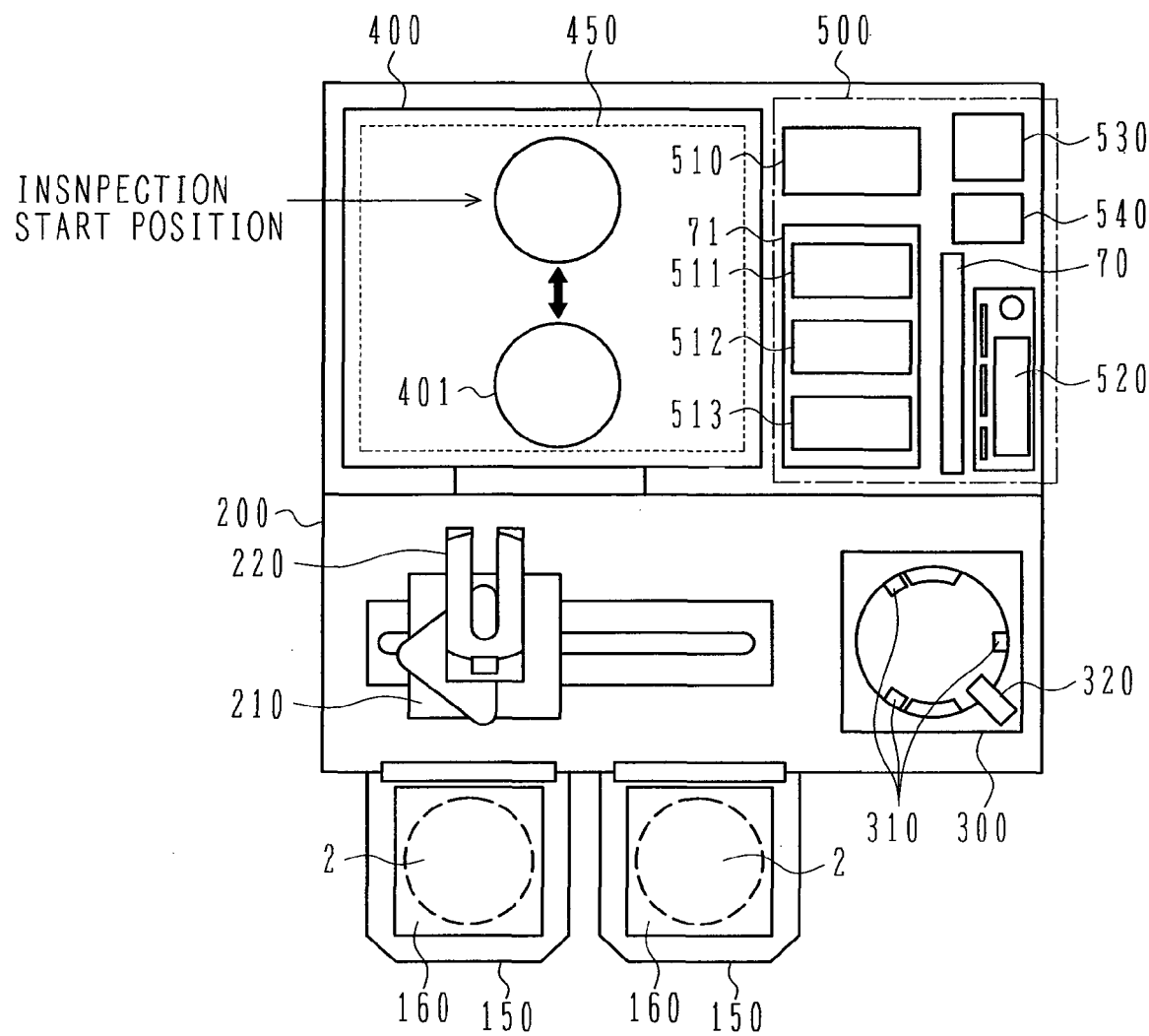
FIG. 6 is a schematic plan view showing the construction of a surface inspection apparatus according to a second embodiment of the present invention.

FIG. 6 schematically shows the construction of the surface inspection apparatus of the second embodiment. The surface inspection apparatus comprises one or more load ports 150 which also serve to support an inspected object (wafer) 2, a carrying section 200, a pre-alignment section 300, an inspection section 400, an optical section 450, an object reversing section (not shown), and a data processing section 500. The optical section 450 including the plane mirror moving mechanisms and the light quantity measuring means, both shown in FIGS. 1 and 3, are disposed above the inspection section 400.

The data processing section 500 comprises a host computer 71, a signal processing section 510, an input device 520 such as a keyboard, a mouse or a touch panel, a monitor (display) 70 such as a CRT or a flat panel display, an output device 530 such as a printer, and an external storage device 540 for controlling external media. The host computer 71 includes a processing unit 511, a storage device 512 such as an HDD, a control unit 513, etc. The plane mirror moving mechanisms and the light quantity measuring means are controlled by the data processing section 500. The diagnosis condition setting means is displayed on the monitor 70, thus enabling the operator to make setting through the input device 520. Thus, the data processing section 500 executes overall control of the surface inspection apparatus in accordance with instructions entered through the input device 520. Further, the data processing section 500 displays the setting conditions, the inspection results, the operating state of the surface inspection apparatus, etc. on the monitor (display) 70, and it also outputs those items to the output device 530.

A pod (cassette) 160 containing a plurality of inspected objects 2 is loaded in each of the load ports 150. The presence or absence of the inspected object 2 on each shelf stage is detected by a position sensor (not shown) disposed near the pod 160, and the loaded position of each inspected object 2 is stored in the storage device 512.

The carrying section 200 drives a carrying apparatus 210 in accordance with an instruction from the data processing section 500. A handling arm 220 disposed on the carrying apparatus 210 grips the inspected object 2 at its edge (beveled edge) and handles it among the pod 160, the pre-alignment section 300, and the inspection section 140.

The pre-alignment section 300 rotates the inspected object 2 while supporting it at an edge thereof by claws 310. An outer peripheral portion of the inspected object 2 is sensed by a sensor 320 for the so-called pre-alignment, i.e., correction of a position deviation of the inspected object 2 and adjustment of a notch position thereon.

The object reversing section (not shown) is disposed near the pre-alignment section 300. When the rear surface of the inspected object 2 is inspected, the inspected object 2 is reversed by the object reversing section such that the rear surface is positioned on the front side.

The inspection section 400 includes an edge-gripping inspection stage 401 which grips the inspected object 2 at its edge. The inspection stage 401 includes a rotation mechanism (θ-direction), an extension/retraction driving mechanism (linear driving mechanism), and lifting/lowering mechanism (Z-direction). Defects on the surface of the inspected object 2 are inspected by scanning the laser beam L1 in a spiral locus while adjusting the focal position with respect to the inspected object 2. Thus, in the surface inspection apparatus of this second embodiment, the inspected object 2 is carried and subjected to the inspection in such a manner that the object surface not inspected (i.e., the rear surface of the inspected object 2) is kept from contacting with the inner surface of a carrying mechanism element. With such a construction, the surface inspection apparatus enables each of the front surface and the rear surface of the inspected object 2 to be inspected.

Figure 7:
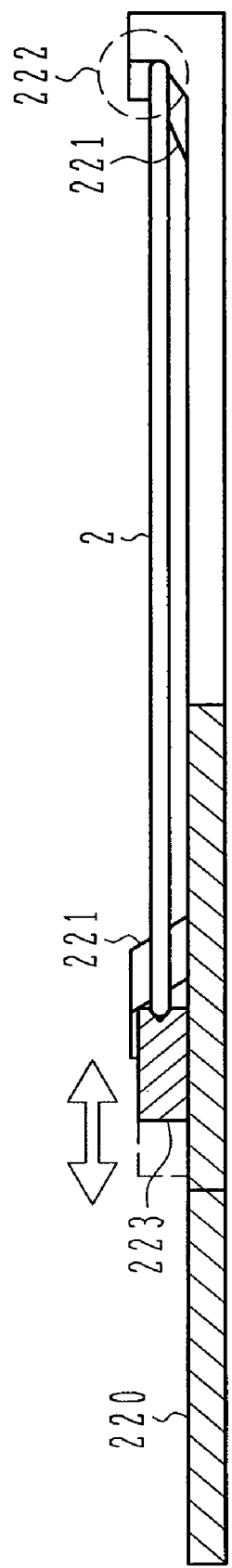
FIG. 7 is a schematic view for explaining a mechanism for gripping an object to be inspected according to the second embodiment of the present invention.
Figure 8:
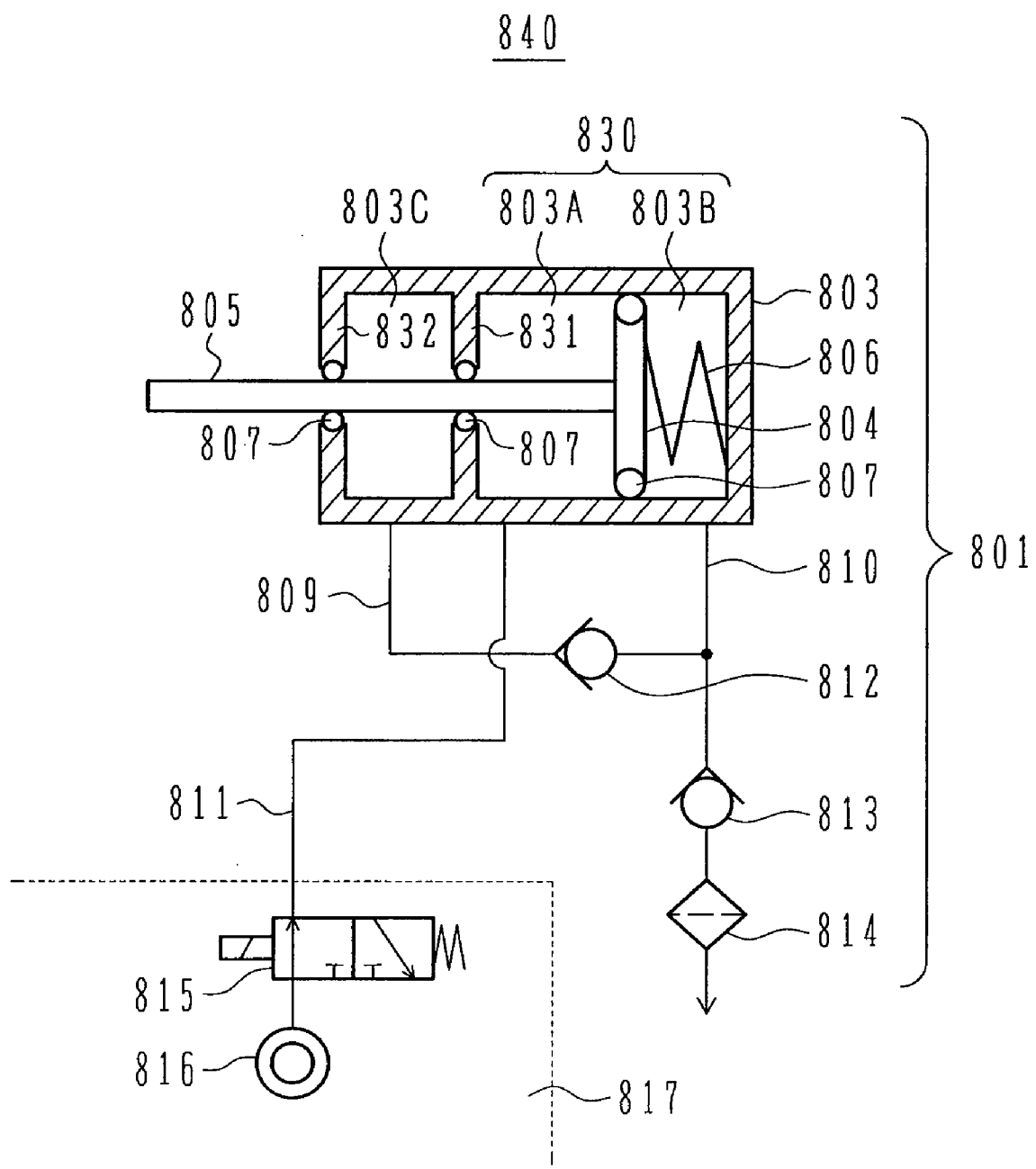
FIG. 8 is a schematic view showing the construction of a linearly reciprocating device according to the second embodiment of the present invention.

FIG. 7 schematically shows the construction of the handling arm 220. The handling arm 220 has a plurality of slopes 221 projected thereon so as to hold the inspected object 2 at its edge. A side wall surface 222 is formed on the front slope 221 of the handling arm 220 such that the edge of the inspected object 2 is stopped while being pressed against the front slope 221. A pressing mechanism 223 for pressing the edge of the inspected object 2 is disposed on the rear side. The inspected object 2 is placed substantially the center among the slopes 221 and is gripped by the handling arm 220 when the object edge is pressed by the pressing mechanism 223. With the provision of such a gripping mechanism, the object surface not inspected (i.e., the rear surface of the inspected object 2) can be carried while being kept from contacting with the inner surface of the handling arm 220.

The pressing mechanism 223 is driven by an actuator for a linearly reciprocating device 840. The linearly reciprocating device 840 is installed in a clean flow area 801. A pressure source (pressurized air pump) 816 and a flow switching solenoid valve 815 are installed in a down flow area 817. The clean flow area 801 means an area with high cleanness in which the surface inspection apparatus is installed and fine dust is very few. The down flow area 817 means environment in which ordinary air conditioning is performed.

The linearly reciprocating device 840 includes a cylinder 803. The cylinder 803 has a piston chamber 830 and a dust collection chamber 803C. A piston 894 is disposed in the piston chamber 830 to be able to slide and reciprocate therein. The piston chamber 830 is divided into two chambers (803A on one side and 803B on the other side) by the piston 804.

Since a biasing spring 806 is built in the chamber 803B, the chamber 803B is called here a biasing spring built-in chamber. Also, the adjacent chamber 803A in which no biasing spring is built is called here a biasing spring not-built-in chamber.

The piston chamber 830 and the dust collection chamber 803C are separated by an adjacent wall (partition) 831. A piston rod 805 fixed to the piston 804 is extended to the outside of the cylinder 803 while penetrating through the adjacent wall 831 and an outer wall 832 of the dust collection chamber 803C.

Seal rings 807 are disposed to seal a gap between an outer peripheral surface of the piston 804 and an inner peripheral surface of the piston chamber 830 and to seal gaps between an outer peripheral surface of the piston rod 805 and inner surfaces of through-holes formed in the adjacent wall 831 and the outer wall 832.

The pressing mechanism 223, shown in FIG. 7, is coupled to the fore end of the piston rod 805, which is extended to the outside of the cylinder 803. With the reciprocating motion of the piston 804, the pressing mechanism 223 is operated through the piston rod 805 such that the inspected object 2 is gripped by or released from the handling arm 220.

The biasing spring 806 is formed of a compression coil spring. With the provision of the compression-type biasing spring 806, the piston 804 is always subjected to a pressing force acting in a direction toward the dust collection chamber 803C. Because the piston 804 is pushed back to move toward the dust collection chamber 803C by the biasing force of the biasing spring 806, the volume of a space in the biasing spring built-in chamber 803B is increased to cause a drop of air pressure therein.

The pressure source (pressurized air pump) 816 for supplying the pressurized air to the biasing spring not-built-in chamber 803A is communicated with the biasing spring not-built-in chamber 803A through a pneumatic tube 811. The flow switching solenoid valve 815 is disposed in the pneumatic tube 811.

A filter 814 for filtering out dust in discharged air is communicated with the biasing spring built-in chamber 803B through a discharge tube 810. The discharged air from which fine dust has been filtered out by the filter 814 is introduced to the clean flow area 801. Since fine dust is filtered out from the discharged air, clean environment in the clean flow area 801 can be held.

A discharge tube 809 for the dust collection chamber 803C communicates the dust collection chamber 803C with the discharge tube 810 or the biasing spring built-in chamber 803B. A check valve 812 for the dust-collection-chamber discharge tube 809 is disposed in the dust-collection-chamber discharge tube 809.

The check valve 812 disposed in the dust-collection-chamber discharge tube 809 checks an air flow directing from the biasing spring built-in chamber 803B toward the dust collection chamber 803C while allowing an air flow to stream in the reversed direction.

A check valve 813 for the discharge tube 810 is disposed in the discharge tube 810. The discharge-tube check valve 813 checks an air flow directing from the filter 814 toward the biasing spring built-in chamber 803B. The discharge-tube check valve 813 is disposed between the filter 814 and a junction at which the dust-collection-chamber discharge tube 809 is connected to the discharge tube 810.

Figure 9B:
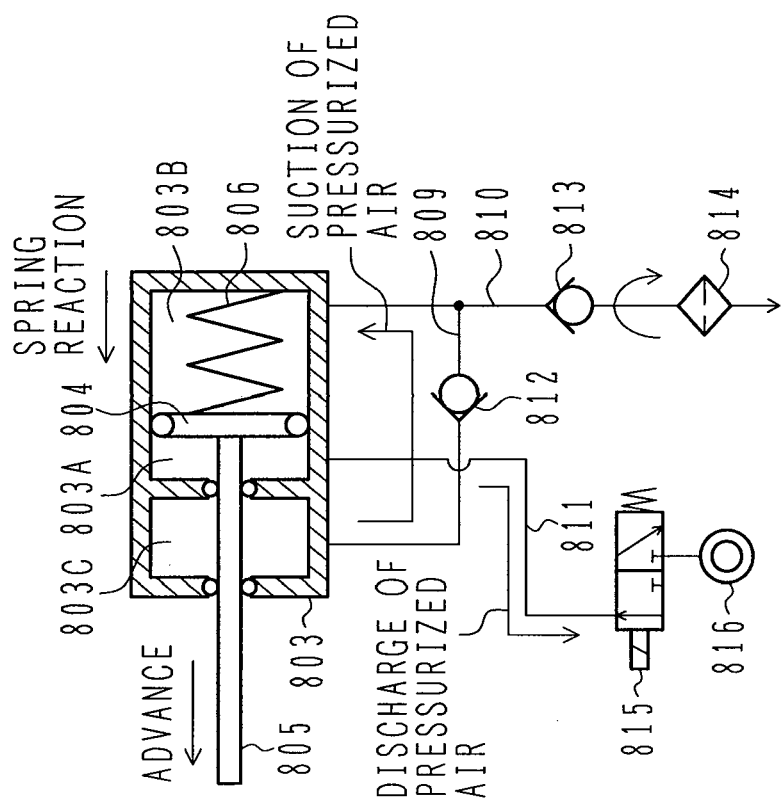
FIGS. 9A and 9B are schematic views for explaining the operation of the linearly reciprocating device according to the second embodiment of the present invention.
Figure 9A:
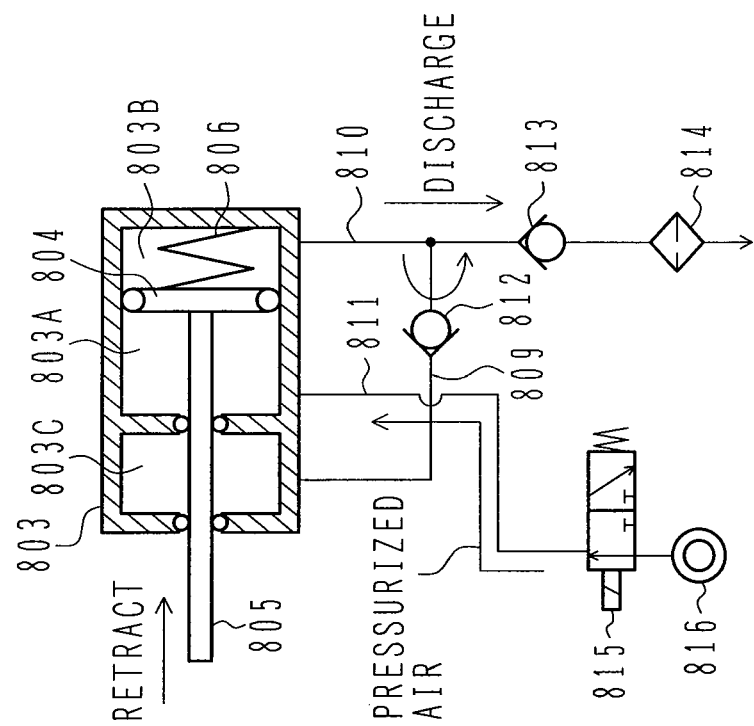

As shown in FIG. 9A, when the flow switching solenoid valve 815 is set to a shift position for supplying the pressurized air and the pressurized air is supplied to the biasing spring not-built-in chamber 803A from the pressure source (pressurized air pump) 816 through the pneumatic tube 811, the piston 804 is moved toward the biasing spring built-in chamber 803B against the biasing force of the biasing spring 806.

With the movement of the piston 804, the volume of the space in the biasing spring built-in chamber 803B is reduced, whereby the gas (air) in the biasing spring built-in chamber 803B is pressurized and discharged to the clean flow area 801 after passing through the discharge tube 810 and the filter 814. Since fine dust in the gas discharged to the clean flow area 801 is filtered out by the filter 814, the clean flow area 801 is not contaminated.

In the state of FIG. 9A, the flow of the discharged air directing from the biasing spring built-in chamber 803B toward the dust collection chamber 803C is checked by the check valve 812 disposed in the dust-collection-chamber discharge tube 809.

As shown in FIG. 9B, when the flow switching solenoid valve 815 is set to a shift position for discharging the pressurized air, the piston 804 is pushed back toward the dust collection chamber 803C by the biasing force of the biasing spring 806 in the compressed state. Therefore, the gas in the biasing spring not-built-in chamber 803A is discharged into the down flow area 817 after passing through the pneumatic tube 811 and the flow switching solenoid valve 815.

With the movement of the piston 804 toward the dust collection chamber 803C, the volume of the space in the biasing spring built-in chamber 803B is increased, whereby the gas pressure in the biasing spring built-in chamber 803B is lowered. Therefore, the gas in the dust collection chamber 803C is sucked into the biasing spring built-in chamber 803B.

Thus, the gas (containing fine dust) having leaked through the seal ring 807 and flown into the dust collection chamber 803C from the biasing spring not-built-in chamber 803A with the supply of the pressurized air is sucked into the biasing spring built-in chamber 803B. As a result, the gas containing fine dust is avoided from leaking into the clean flow area 801 from the cylinder 803, whereby the environment in the clean flow area 801 can be maintained in a satisfactory clean state.

In the state of FIG. 9B, the gas flow directing toward the biasing spring built-in chamber 803B through the filter 814 and the discharge tube 810 is blocked by the discharge-tube check valve 813. Accordingly, a suction force generated in the biasing spring built-in chamber 803B acts only to suck the gas in the dust collection chamber 803C, thus ensuring satisfactory suction of the gas in the dust collection chamber 803C. In other words, an inexpensive apparatus can be realized because of no need of the vacuum source 821 and the line 819 for evacuation, which are required in the related art described above. Further, with the omission of the vacuum source 821 and the line 819 for evacuation, the apparatus can be made more compact. While the illustrated embodiment uses the compression-type biasing spring, a tension spring may be used instead. In the case using a tension spring, it is built in the biasing spring not-built-in chamber 803A.

Figure 10:
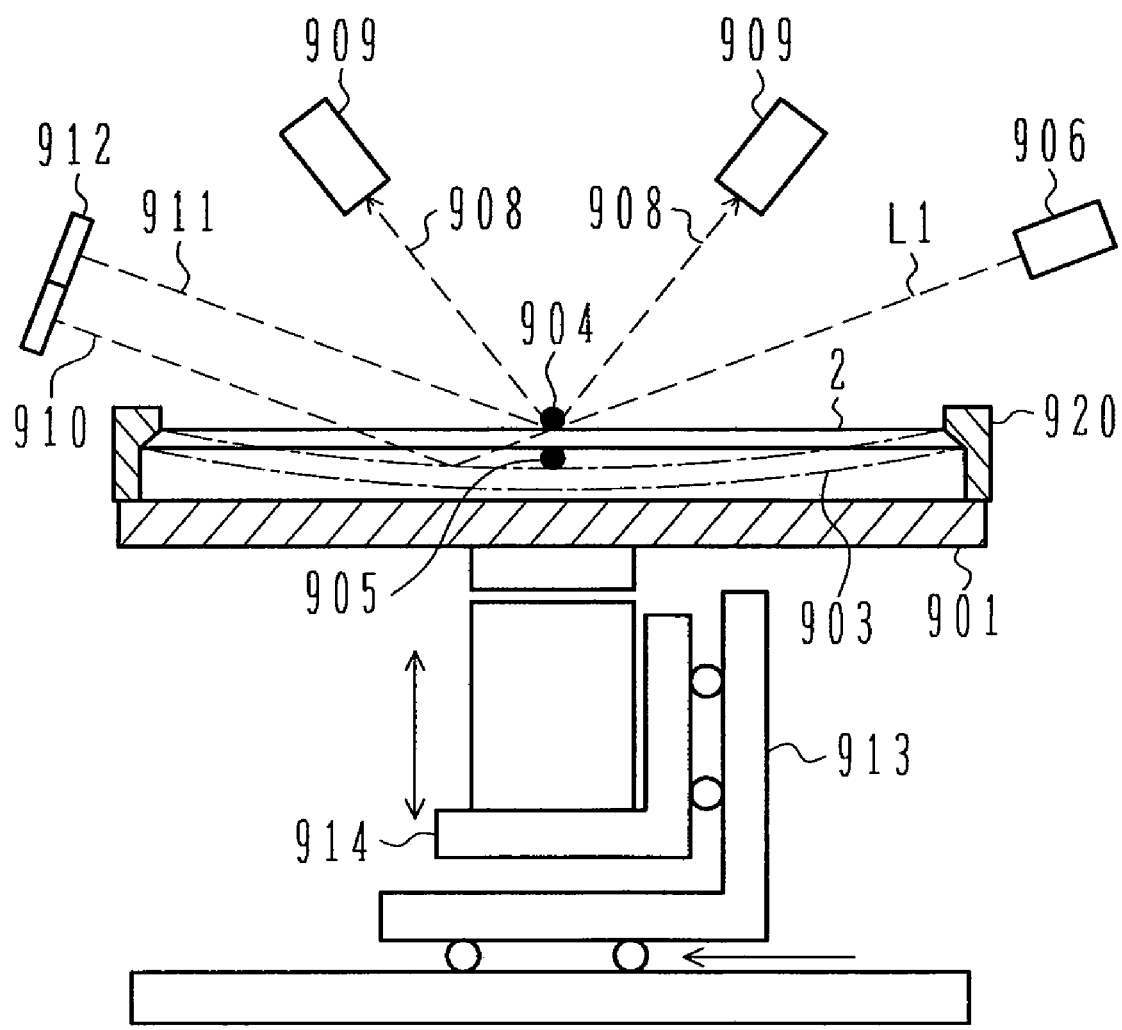
FIG. 10 is a schematic view showing the construction of a wafer surface inspection apparatus according to the second embodiment of the present invention.

FIG. 10 is a schematic sectional view showing the construction of the edge-gripping inspection stage 401 disposed in the inspection section 400. The inspected object 2 gripped by the handing arm 220 is placed substantially the center of an inspection table 901 (inspected object holding means). The inspection table 901 has a chuck 920 for holding an outer peripheral edge of the inspected object 2.

Figure 11:
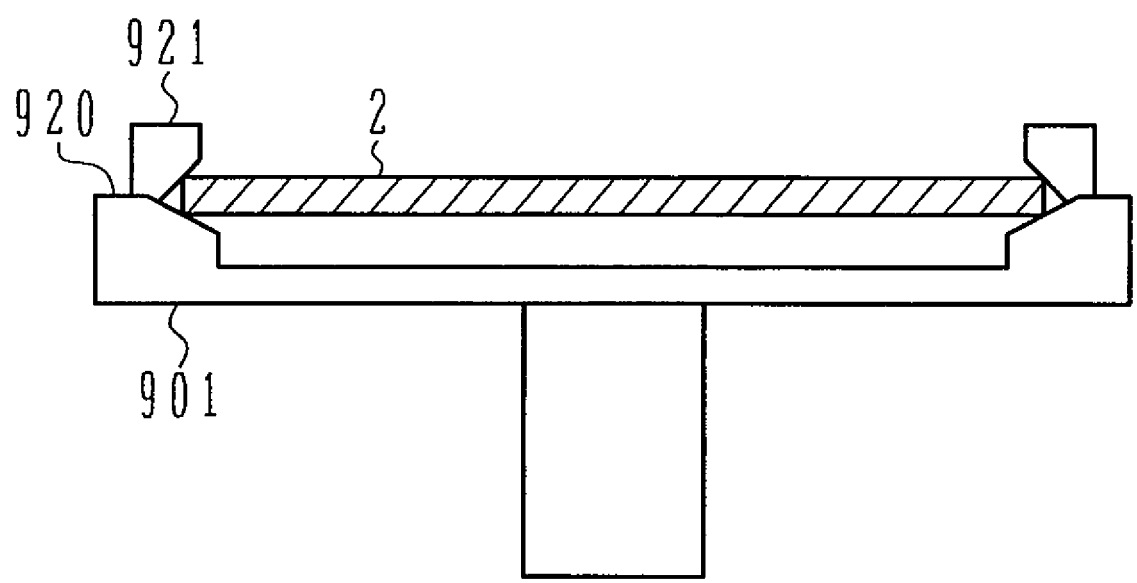
FIG. 11 is a schematic view showing a chuck of an inspected-object holding unit according to the second embodiment of the present invention.

As shown in FIG. 11, the chuck 920 has holding claws 921 which can slide back-and-forth away from and toward the inspection table 901. The holding claws 921 engage with the outer peripheral edge of the inspected object 2, to thereby hold the inspected object 2. By moving back the holding claws 921 outward in the radial direction, the inspected object 2 is released from the held state.

On the inspection table 901, though not shown, there is disposed a flexure adjusting means for controlling the pressure (flow rate) of gas sprayed toward the rear surface of the inspected object 2 (inspection target) and adjusting a flexure of the inspected object 2. The flexure adjusting means may include a regulator or a needle valve for adjusting the pressure or the flow rate of the gas through an orifice, and a mass flow controller for automatically controlling the gas flow rate.

The laser beam L1 (illumination light) having the proper beam status such as the state of polarization and the beam diameter, which has been controlled in the optical section 450, is emitted from a light illumination unit 906 (light illumination means) shown in FIG. 10. When the laser beam L1 is illuminated to the surface of the inspected object 2, a scattered light 908 is generated from a foreign mater 904 on the inspected object 2 upon the illumination of the laser beam L1, and the scattered light 908 is detected by a detector 909 (first light detecting means in the optical system) adapted for the scattered light.

Assuming that the focal position of the optical system is set to the same height (level) as the surface of the inspected object 2, in the case of an inspected object 903 having a flexure as indicated by two-dot-chain lines, a foreign matter 905 on the inspected object 903 comes into a state deviated from the focal position, whereby the detection sensitivity and the accuracy of position coordinates are degraded. To overcome that problem, the surface inspection apparatus of this second embodiment includes a focal position aligning means comprising a vertically driven stage (lifting/lowering mechanism) 914, a reflected-light detector 912 (second light detecting means), the light illumination unit 906 (light illumination means), a focal position alignment control means, a flexure adjusting means, etc., which will be described below.

The focal position aligning means is featured in that it also serves as the light illumination unit 906 (defect detecting means) for detecting foreign matters and defects, and that a regularly reflected light is used in the focal position aligning means, while a scattered light is used in the defect detecting means.

Because the inspected object 2 and the inspected object 903 having a flexure differ from each other in height at their surfaces, reflected lights from both the inspected objects advance along different paths as indicated by a reflected light 910 from the inspected object 2 and a reflected light 911 from the inspected object 903. By detecting such a change in the path between the reflected light 910 and the reflected light 911 with the reflected-light detector 912 (second light detecting means), information about the surface heights of the inspected object 2 and the inspected object 903 having a flexure differ can be obtained. The reflected-light detector 912 may be any type of sensor, e.g., a 2-division sensor, a position sensor, or a sensor using the knife edge method, so long as it is able to provide necessary height information of the object surfaces.

In the inspected object 903 having a flexure, the surface height of the inspected object 903 in the light illuminated position is changed with the movement of a horizontally driven stage 913. Based on such a change, the height information of the surface of the inspected object 903 is detected by the reflected-light detector 912 and the vertically driven stage 914 is moved following the height change of the surface of the inspected object 903. A reduction in both the detection sensitivity and the accuracy of position coordinates can be suppressed by thus correcting the surface height of the inspected object 903 so that the surface of the inspected object 903 in the light illuminated position is always matched with the focal position in the vertical direction.

Herein, the horizontally driven stage (back-and-forth moving mechanism) 913 and the vertically driven stage (lifting/lowering mechanism) 914 are called together an inspected object moving means. The horizontally driven stage 913 provides the inspected object moving means with the function of carrying the inspected object in the horizontal direction, and the vertically driven stage 914 provides the inspected object moving means with the function of moving the inspected object in the vertical direction.

The entire surface of the inspected object 2 can be inspected along a spiral or circular locus by moving the inspected object 2 in one direction with the horizontally driven stage 913 of the inspected object moving means while the inspected object 2 is rotated (by the rotation driving mechanism). Also, the focal position can be correctly aligned by vertically moving the inspected object with the vertically driven stage 914 of the inspected object moving means.

Figure 12:
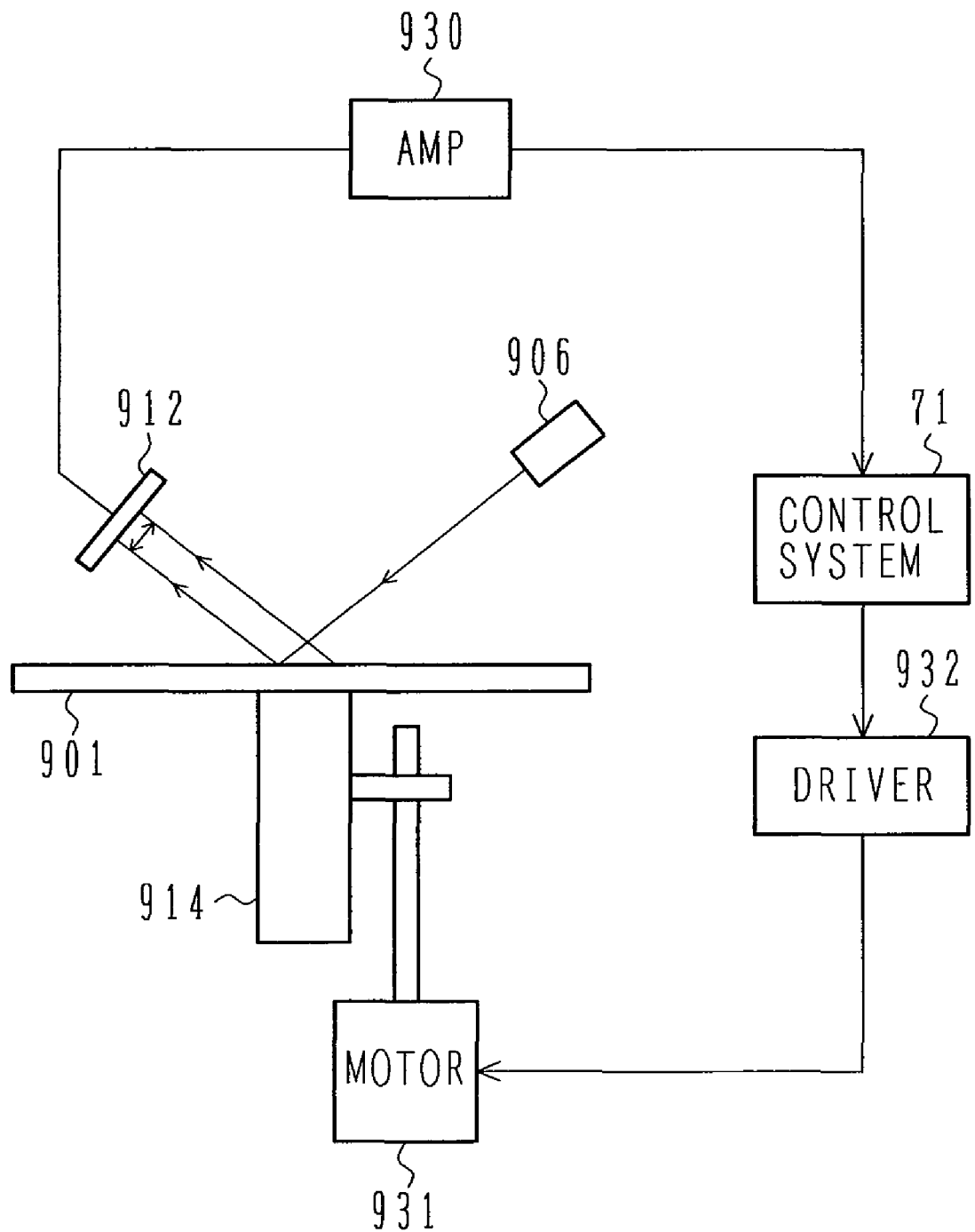
FIG. 12 is a circuit diagram for explaining control of the height of the inspected object surface, which is performed by feed-backing information about the height of the inspected object surface to a control system.

A method of correctly aligning the focal position will be described in more detail below with reference to FIG. 12. The focal position aligning means includes a focal position alignment control means comprising a motor 931, a driving controller (driver) 932, the host computer 71, and an amplifier 930.

A signal representing the height information of the surface of the inspected object 2, which is detected by the detector 912 serving as the second light detecting means, is amplified by the amplifier 930 and is fed back to the host computer 71. The host computer 71 calculates a correction value based on the received signal, and the motor 931 for driving the vertically driven stage 914 is controlled by the driver 932 in accordance with the calculated correction value. As a result, the vertical position of the surface of the inspected object 2 is adjusted to be kept in match with the focal position of the first light detecting means in the optical system. Since the focal position of the first light detecting means in the optical system is always correctly aligned, the foreign matter and the defect on the inspected object 2 can be inspected with high accuracy regardless of whether the inspected object 2 has a flexure or not.

Further, since the light illumination unit 906 (light illumination means) for detecting foreign matters and defects are used to serve also as the focal position aligning means, it is possible to simplify the apparatus configuration and to reduce the production cost.

The alignment of the focal position can also be performed in combination of the vertical movement of the inspection table 901 (inspected object holding means) and the adjustment made by the above-mentioned flexure adjusting means. Thus, since foreign matters and defects are inspected under the proper alignment of the focal position at all times without contacting the rear surface of the inspected object 2 with the inspected object 2, the front and rear surfaces of the inspected object can be inspected with high sensitivity and satisfactory coordinate accuracy without suffering from a variation of sensitivity.

Optimization of the light quantity of the reflected light received by the second light detecting means will be described below with reference to FIG. 13.

Figure 13A:
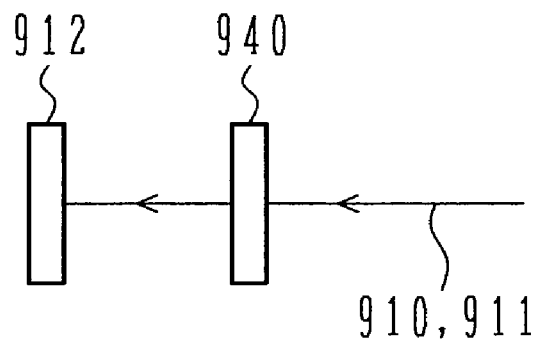
FIGS. 13A and 13B are schematic views showing light quantity adjusting unit according to the second embodiment of the present invention.
Figure 13B:
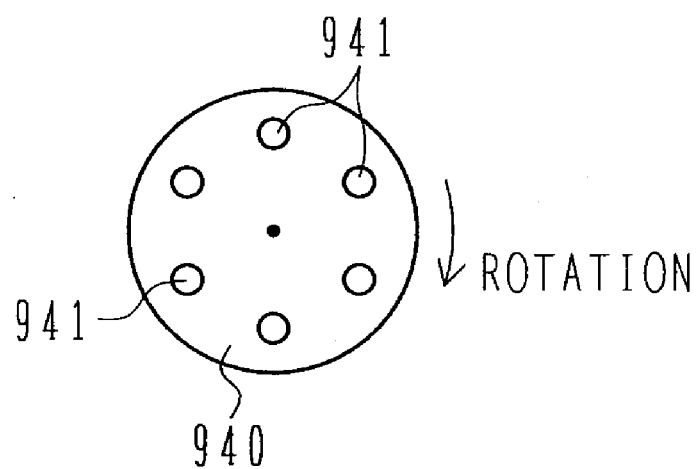
Figure 14:
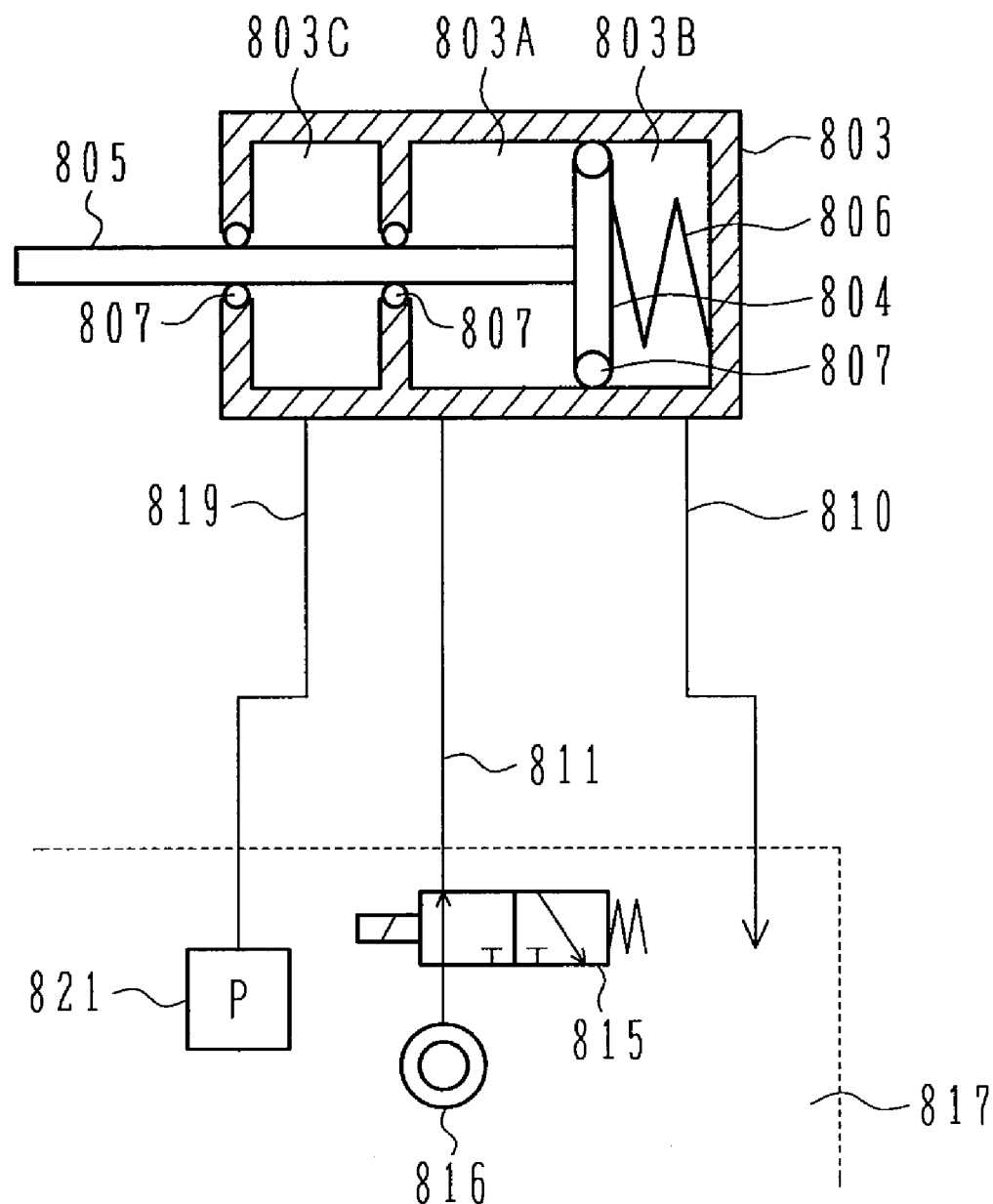
FIG. 14 is a schematic view of a known linearly reciprocating device.

As shown in FIG. 13A, the reflected lights 910 and 911 from the surfaces of the inspected object 2 and the inspected object 903 having a flexure pass through an ND filter 940 (light quantity adjusting means) and is received by the detector 912 (second light detecting means). As shown in FIG. 13B, the ND filter 940 includes one or more optical elements (light quantity adjusting elements) 941.

The light quantities of the reflected lights 910 and 911 differ depending on the type and thickness of a film formed on the inspected object, and such a variation of the light quantities makes unstable the detection performed by the detector 912 (second light detecting means). To avoid that problem, the ND filter 940 is constructed such that it is rotatable to allow selection of proper one of the optical elements 941, which optimizes the detection performed by the detector 912. By using the ND filter 940 of that rotatable structure, inspected objects having various film types and thicknesses can also be inspected with performance comparable to that obtained when the inspected object having no films is inspected. In addition, by correctly aligning the focal position with the aid of the ND filter 940, even inspected objects differing in thicknesses, crystal azimuth, warp, etc. can be inspected with performance comparable to that obtained when a standard inspected object (wafer) is inspected. The ND filter 940 (light quantity adjusting means) includes a mechanism (not shown) for driving the light quantity adjusting means. In accordance with a signal detected by the detector 912, the host computer 71 controls the mechanism for driving the light quantity adjusting means so that the light quantity is adjusted to an optimum value (with the function of the light quantity control means).

A processing flow in the surface inspection apparatus of the second embodiment will be described below. The inspected object 2 carried out from the pod 160 is carried into the pre-alignment section 300 by the carrying apparatus 210 and gripped by the claws 310.

When the inspection mode is set to a mode of inspecting the rear surface of the inspected object 2, the inspected object 2 is carried to the object reversing section in the course of carrying toward the pre-alignment section 300 and is gripped by the claws 310 after the inspected object 2 has been reversed such that the rear surface is positioned on the front side.

On the other hand, the host computer 71 controls the plane mirror moving mechanisms 40a and 40b and the light quantity measuring means of the optical section 450 in accordance with an instruction from the diagnosis condition setting means 80, shown in FIG. 4, whereby the plane mirrors 4a and 4b are moved and the light quantity of the laser source 3 is adjusted so as to stabilize the illumination intensity of the laser beam L1.

In the pre-alignment section 300, the inspected object 2 is subjected to the so-called pre-alignment, i.e., correction of its position deviation and adjustment of a notch position thereon. After the pre-alignment, the inspected object 2 is handled again by the carrying apparatus 210 and is carried to the inspection stage 401 in the inspection section 400. On that occasion, the linearly reciprocating device 840 disposed in the carrying apparatus minimizes the amount of dust generated due to sliding motion of the linearly reciprocating device 840 and suppresses an increase of foreign matters generated in the carrying step.

The inspected object 2 placed on the inspection table 901 of the inspection stage 401 is fixedly supported on the inspection stage 401 with the outer peripheral edge of the inspected object 2 gripped by the holding claws 921.

The inspection stage 401 including the inspected object 2 set thereon is moved to an inspection start position while its rotational speed is gradually increased by the rotation driving mechanism. At the time when the rotational speed of the inspection stage 401 reaches a predetermined speed, the surface inspection of the inspected object 2 is started.

The laser beam L1 having the proper beam status controlled by the optical section 450 is emitted through the light illumination unit 906. The laser beam L1 having been illuminated to and regularly reflected by the inspected object 2 is received by the reflected-light detector 912, and height information (electric signal) of the surface of the inspected object 2 is amplified by the amplifier 930 and transmitted to the host computer 71.

The host computer 71 calculates a correction value for the object position in the vertical direction based on the received signal, and then drives the vertically driven stage 914 through the driver 932 and the motor 931, thereby controlling the height (vertical position) of the surface of the inspected object 2 to be always kept in match with the focal position of the laser beam L1 (with the function of the focal position aligning means).

The scattered light generated by a foreign matter or a defect on the surface of the inspected object 2 is received by the scattered-light detector 909. A signal from the detector 909 is processed by the data processing section 500 in correlation to position information obtained from the rotation driving mechanism and the horizontally driven mechanism 913, and the size and position coordinates of the foreign matter or the defect are calculated. The calculated size and position coordinates of the foreign matter or the defect are stored in the storage device 512 and are outputted to the monitor 70 and/or the output device during or after the surface inspection of the inspected object 2.

With both the rotation given by the rotation driving mechanism and the linear motion given by the horizontally driven mechanism 913 in the direction of one axis, the laser beam L1 is scanned over the surface of the inspected object 2 along a spiral or circular locus. The focal position aligning means always adjusts the surface of the inspected object 2 to be matched with the focal position of the laser beam L1 while tracking height change of the surface of the inspected object 2, which is caused with the scan of the laser beam L1, in order to stabilize the detection sensitivity and the accuracy of position coordinates of foreign matters and defects. After completion of the inspection, the inspected object 2 is handled by the carrying apparatus 210 and is returned to the same shelf stage of the pod 160 as that from which the inspected object 2 was carried out, through procedures reversal to the above-described ones.

While the embodiments have been described in connection with the defect inspection apparatus and the surface inspection apparatus for detecting defects (such as foreign matters, contaminations, cracks, crystal defects, COP (crystal originated particle), and pattern defects) of inspected objects by using the laser beam, the present invention is not limited to those apparatuses. The present invention can also be applied to a foreign-matter inspection apparatus, a disk inspection apparatus, and so on.

Further, the optical system embodying the present invention is not limited to one using the laser beam, and the present invention is similarly applied to a variety of other optical systems using a halogen lamp, a mercury lamp, a Xe lamp, and so on. In other words, the present invention can be applied to any type of inspection apparatuses using light, such as an appearance inspection apparatus, a mask inspection apparatus, and a bevel inspection apparatus. The linearly reciprocating device used in the embodiments can be widely applied to processing apparatuses and manufacturing apparatuses in addition to inspection apparatuses.

Further, a reflecting mirror is used as the plane mirror 4a or 4b in the described embodiments, but the present invention is not limited thereto, and, another type of mirror such as a convex mirror or a concave mirror may be similarly used instead of the plane mirror.

What is claimed is:

1. An optical defect inspection apparatus comprising:
   a light illuminating unit for illuminating a light to an object to be inspected;
   a first light detecting unit of an optical system for detecting a light scattered from the inspected object;
   an inspected object moving unit for moving the inspected object such that a position on the inspected object illuminated by the light from the light illuminating unit is changed;
   an inspected object holding unit for holding the inspected object; and
   a focal position aligning unit for detecting the light illuminated from the light illuminating unit and reflected by the inspected object, obtaining height information of a surface of the inspected object, and aligning a focal position of the first light detecting unit of the optical system based on the obtained information,
   wherein the focal position is aligned by combined control of an operation of vertically moving the inspected object holding unit and an operation of spraying the gas toward the rear surface thereof.

2. The optical defect inspection apparatus according to claim 1, where the focal position aligning unit includes a second light detecting unit for detecting the light illuminated from the light illuminating unit and reflected by the inspected object, and a control system for executing control based on height information, which is detected by the second light detecting unit and is fed back, such that the focal position and the surface of the inspected object are held at the same height.

3. The optical defect inspection apparatus according to claim 1, wherein said optical defect inspection apparatus further comprises a light quantity optimizing unit for optimizing a quantity of the reflected light from the inspected object by an optical element.

4. The optical defect inspection apparatus according to claim 1, wherein the inspected object is supported at an outer peripheral edge thereof by the inspected object holding unit, thereby enabling the inspected object to be inspected while a rear surface of the inspected object is kept in a non-contact state.

5. The optical defect inspection apparatus according to claim 1, wherein the inspected object is two-dimensionally moved by moving the inspected object in one direction while the inspected object is rotated.

* * * * *